US012570825B2

(12) United States Patent
Edmundson et al.

(10) Patent No.: US 12,570,825 B2
(45) Date of Patent: Mar. 10, 2026

(54) COMPOSITE MATERIAL INCLUDING A HIERARCHICAL AND NANOPOROUS METAL IN POROUS POLYMER SUBSTRATE

(71) Applicant: W. L. Gore & Associates, Inc., Newark, DE (US)

(72) Inventors: Mark D. Edmundson, Rancho Palos Verdes, CA (US); Phuong Q. Hua, Flagstaff, AZ (US); Corey A. Abrams, Weehawken, NJ (US); Rochitha R. Nathan, Philadelphia, PA (US)

(73) Assignee: W. L. Gore & Associates, Inc., Newark, DE (US)

( * ) Notice: Subject to any disclaimer, the term of this patent is extended or adjusted under 35 U.S.C. 154(b) by 321 days.

(21) Appl. No.: 18/287,243

(22) PCT Filed: Apr. 14, 2022

(86) PCT No.: PCT/US2022/024869
§ 371 (c)(1),
(2) Date: Oct. 17, 2023

(87) PCT Pub. No.: WO2022/225790
PCT Pub. Date: Oct. 27, 2022

(65) Prior Publication Data
US 2024/0199836 A1    Jun. 20, 2024

Related U.S. Application Data

(60) Provisional application No. 63/326,593, filed on Apr. 1, 2022, provisional application No. 63/176,669, filed on Apr. 19, 2021.

(51) Int. Cl.
*C08J 9/40* (2006.01)
*A61B 5/1468* (2006.01)
(Continued)

(52) U.S. Cl.
CPC ............ *C08J 9/40* (2013.01); *G01N 27/3278* (2013.01); *A61B 5/1468* (2013.01);
(Continued)

(58) Field of Classification Search
None
See application file for complete search history.

(56) References Cited

U.S. PATENT DOCUMENTS

| 4,972,846 A | 11/1990 | Owens et al. |
| 5,269,810 A | 12/1993 | Hull et al. |
| | (Continued) | |

FOREIGN PATENT DOCUMENTS

| KR | 10-2019-0113539 A | 10/2019 |
| TW | 201122468 A | 7/2011 |
| | (Continued) | |

OTHER PUBLICATIONS

Composites of Nanoporous Gold and Polymer, by Wang et al., Advance Materials 2013 (Year: 2013).*
(Continued)

*Primary Examiner* — Yan Lan

(57) ABSTRACT

A composite material is disclosed including a porous polymer substrate and a nanoporous metal present within the microporous polymer substrate. The nanoporous metal may have a hierarchical structure. The nanoporous metal may have a unimodal and right-skewed number-based nanopore size distribution. The porous polymer substrate may support tissue integration and/or tissue ingrowth in certain applications. The composite material may be used in electrochemical analyte biosensors and other applications.

24 Claims, 26 Drawing Sheets

(51) Int. Cl.
  *G01N 27/327*  (2006.01)
  *H01M 8/16*   (2006.01)
(52) U.S. Cl.
  CPC ... *A61B 2562/0285* (2013.01); *C08J 2327/18*
      (2013.01); *H01M 8/16* (2013.01)

(56) References Cited

U.S. PATENT DOCUMENTS

| | | | |
|---|---|---|---|
| 5,910,354 A | 6/1999 | Meola et al. | |
| 9,018,264 B2 | 4/2015 | Freese | |
| 2004/0122509 A1 | 6/2004 | Brodeur | |
| 2010/0030308 A1 | 2/2010 | Anderson et al. | |
| 2011/0172116 A1* | 7/2011 | Dutta .................. | G01N 33/544 |
| | | | 506/13 |
| 2012/0202043 A1* | 8/2012 | Bonn-Savage ........ | A01N 59/16 |
| | | | 977/788 |
| 2013/0236502 A1 | 9/2013 | Marshall et al. | |
| 2017/0173535 A1* | 6/2017 | Jiang .................. | B01D 67/0069 |
| 2020/0003754 A1 | 1/2020 | Daniels et al. | |
| 2020/0046273 A1 | 2/2020 | Simpson et al. | |

FOREIGN PATENT DOCUMENTS

| | | | |
|---|---|---|---|
| WO | 2019/216885 A1 | 11/2019 | |
| WO | 2020/037269 A2 | 2/2020 | |
| WO | 2022/225792 A1 | 10/2022 | |

OTHER PUBLICATIONS

Alexander et al., "Gold-Containing Polytetrafluoroethylene Modified by Ketoprofen: Synthesis and Spectroscopic Characterization", SGEM, vol. 19, No. 6.3, 2019, pp. 1-1.

International Preliminary Report on Patentability received for PCT Patent Application No. PCT/US2022/024869, mailed on Nov. 2, 2023, 8 pages.

International Search Report and Written Opinion received for PCT Patent Application No. PCT/US2022/024869, mailed on Jul. 15, 2022, 10 pages.

Detisch et al., "Nanoporous metal—polymer composite membranes for organics separations and catalysis", Journal of Materials Research, Vol. 35, No. 19, pp. 2629-2642.

Griffiths et al., "Nanoporus metal based composites: Giving polymers strength and making metals move", Journal of the Mechanics and Physics of Solids, Vol. 137, No. 1, Apr. 2020, pp. 1-18.

Halik et al., "On the porosity of polypyrrole films", Synthetic Metals, Vol. 157, No. 24, Dec. 2007, pp. 1085-1090.

Mao et al., "A Porous and Interconnected Polypyrrole Film with High Conductivity and Ion Accessibility as Electrode for Flexible All-Solid-State Supercapacitors", ChemElectroChem, Vol. 6, No. 21, 2019, pp. 5479-5485.

Vukovic et al., "Supramolecular Route to Well-Ordered Metal Nanofoams", ACS Nano, Vol. 5, No. 8, 2011, pp. 6339-6348.

* cited by examiner

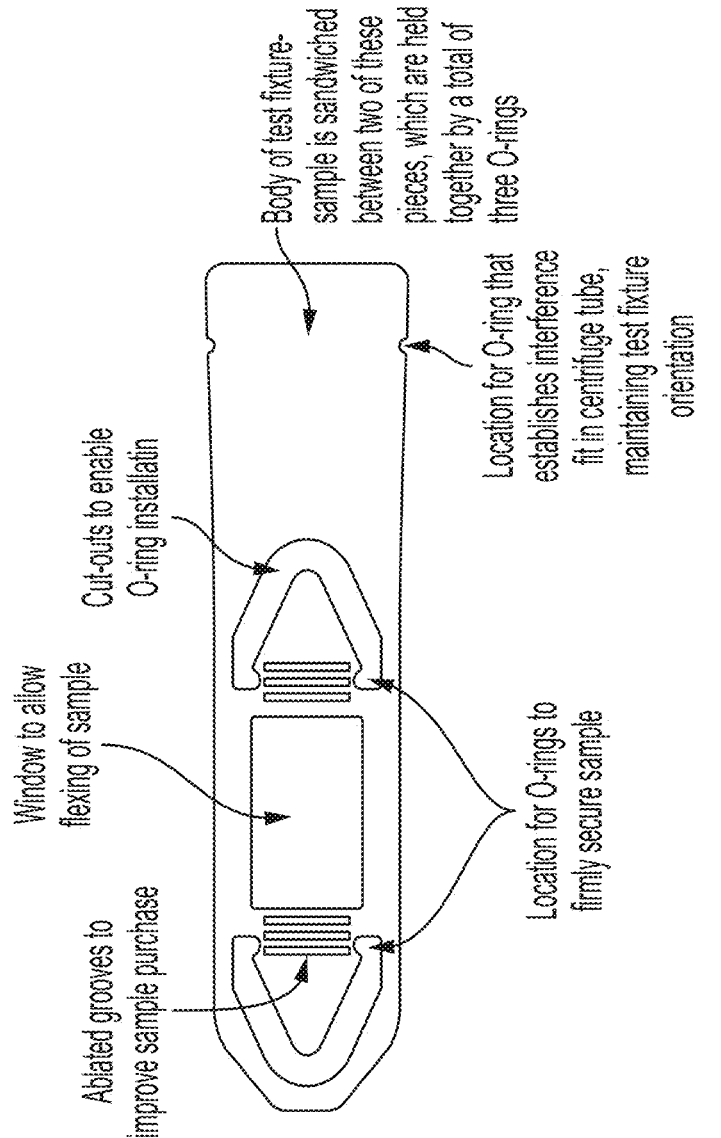

Body of test fixture-sample is sandwiched between two of these pieces, which are held together by a total of three O-rings Location for O-ring that establishes interference fit in centrifuge tube, maintaining test fixture orientation Out-outs to enable O-ring installatin Window to allow flexing of sample Location for O-rings to firmly secure sample Ablated grooves to improve sample purchase

*Fig. 13*

COMPOSITE MATERIAL INCLUDING A HIERARCHICAL AND NANOPOROUS METAL IN POROUS POLYMER SUBSTRATE

CROSS-REFERENCE TO RELATED APPLICATION

This application is a national phase application of PCT Application No. PCT/US2022/024869, internationally filed on Apr. 14, 2022, which claims the benefit of Provisional Application No. 63/176,669, filed Apr. 19, 2021, and also claims the benefit of Provisional Application No. 63/326,593, filed Apr. 1, 2022, which are incorporated herein by reference in their entireties for all purposes.

FIELD

The present disclosure relates generally to a composite material including a hierarchical and nanoporous metal phase within a porous polymer substrate, and associated methods of making and using such materials.

BACKGROUND

Nanoporous metals have been studied extensively for a wide range of applications, including enzyme-based biosensors and biofuel cells. This interest has been driven by a combination of properties including electrical conductivity, high metal surface area, and nano-scale pores. Collectively, these properties have enabled nanoporous metals to excel when converted into electrodes in lab-scale benchtop or in vivo experiments. These electrodes have exhibited much higher electrochemical surface area compared to metal foils, as well as higher signal response (e.g., for sensors) or higher current density normalized to geometric area (e.g., for biofuel cells). They have also demonstrated greater retention of electrochemical signals in the presence of biofouling agents such as albumin and fibrinogen. This phenomenon is generally referred to as "biofouling resistance" and has been attributed to size exclusion of the biofouling agents by the nanoscale pores. However, despite strong interest and development for over a decade, nanoporous metals still exhibit limitations that have prevented significant commercialization.

A first limitation of traditional nanoporous metals is their relatively poor mechanical properties. Nanoporous metals are brittle and tear easily, which makes handling and processing difficult. Their fragility also raises concerns about long-term durability in the targeted applications. Their mechanical properties may limit how thin these materials can be made (typically around 100 μm) before they must be placed on a carrier film, such as polyethylene terephthalate (PET). The use of these carrier films is often undesirable because they block mass transfer to and from one side of the nanoporous metal. The carrier films can also cause stability issues in the targeted applications, particularly in vivo applications, or those that require exposure to high temperatures or challenging chemical environments.

A second limitation of traditional nanoporous metals is the cumbersome and wasteful process by which they are typically produced. The standard process comprises de-alloying metal foils, which typically involves the use of hazardous chemicals such as strong mineral acids. It is also an inherently subtractive process and is therefore wasteful. The de-alloying also results in significant volume contraction of the foil, which may complicate its use with multi-layer composites because it increases interfacial stresses, which can cause delamination and/or warping. Furthermore, cutting the foils to produce complex shapes, often desired in applications such as sensors, is again a subtractive process, and therefore wasteful.

A final limitation of traditional nanoporous metals is the size of the nanopores themselves, which while advantageous in some contexts, can be highly limiting in others. For example, mass transfer into nanoscale pores can be highly limited, making it difficult to take advantage of the high internal surface area for active sites for electrochemical reactions. As another example, nanoscale pores are typically too small to permit tissue ingrowth and vascularization, which may be desirable in some in vivo applications.

SUMMARY

The present disclosure provides a composite material including a porous polymer substrate and a nanoporous metal present within the microporous polymer substrate. The nanoporous metal may have a hierarchical structure. The nanoporous metal may have a unimodal and right-skewed number-based nanopore size distribution. The porous polymer substrate may support tissue integration and/or tissue ingrowth in certain applications. The composite material may be used in electrochemical analyte biosensors and other applications. The present disclosure addresses one or more of the limitations of traditional nanoporous metals using porous polymer substrates.

According to an exemplary embodiment of the present disclosure, a composite material is disclosed including a porous polymer substrate and a nanoporous metal present within the porous polymer substrate and including a number-based nanopore size distribution and a volume-based nanopore size distribution, wherein an average of the volume-based pore size distribution is at least 200% greater than an average of the number-based nanopore size distribution.

According to another exemplary embodiment of the present disclosure, a composite material is disclosed including a microporous polymer substrate including a plurality of interconnected micropores and a nanoporous metal at least partially contained in the micropores of the microporous polymer substrate and separated from the microporous polymer substrate to define gaps.

According to yet another exemplary embodiment of the present disclosure, a composite material is disclosed including a first continuous network including a microporous polymer having a plurality of interconnected micropores, and a second substantially continuous network including a nanoporous metal, the second substantially continuous network interpenetrating the first continuous network, wherein the composite material has a porosity of at least 30 vol. %.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIGS. 13-15 depict a wet flex particulation durability test method;

DEFINITIONS

Figure 1:
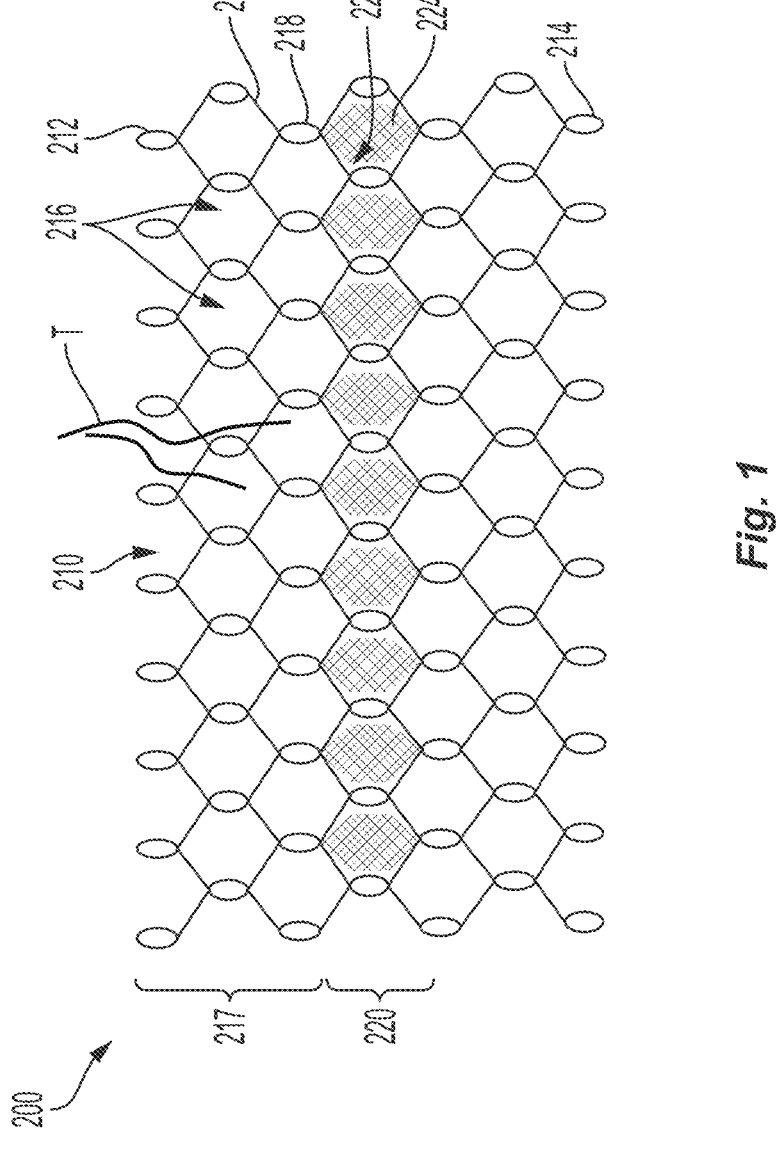
FIG. 1 is a cross-sectional view of a composite material of the present disclosure.

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example. In the event it is determined that individuals having ordinary skill in the relevant arts would not readily ascertain values for such reasonably small differences, the terms "about" and "approximately" can be understood to mean plus or minus 10% of the stated value.

As used herein, the phrase "tissue integration" refers to exposing a device to surrounding tissue while minimizing deleterious reactions in surrounding tissue such as inflammation and encapsulation that may compromise the intended performance of the device over the intended period of use. Essentially, and without wishing to be bound by theory, the device reaches a biocompatible quiescent state in the surrounding tissue.

As used herein, the phrase "tissue ingrowth" refers to growth of tissues, cells, capillaries, and/or other bodily components into a full thickness or a partial thickness of a porous material.

As used herein, the term "microporous" refers to a material that comprises pores of a single pore size or of a distribution of pore sizes. The average pore size may be about 0.1 μm to about 50 μm. It will be understood that the microporous material may include individual pores that fall outside of this average size range, including some macropores. The microporous material may have a characteristic or nominal pore size characterized by bubble point analysis or another suitable test, as set forth below. The average pore size of the membrane may, for example, be characterized by the mean flow pore size determined by capillary flow porometry.

As used herein, the term "nanoporous" refers to a material that comprises pores of a single pore size or of a distribution of pore sizes. The number-based average pore size may be about 1 nm to about 500 nm. Said distributions can comprise multiple populations of pores with different sizes in the range of about 1 nm diameter to about 10 nm, about 10 nm to about 100 nm, or about 100 nm to about 500 nm. It will be understood that the nanoporous material may include individual pores that fall outside of these size ranges, including some micropores. The pore size may be characterized by quantitative image analysis, as set forth below.

As used herein, the term "conformal" refers to a coating layer which coats interior surfaces of an underlying porous substrate. In embodiments where the coating layer includes an electrically conductive material, the conformal coating may achieve electrical conductivity through and along the surface of the coating layer.

As used herein, the term "imbibed" refers to a material that is deposited within the pores of a porous substrate using a fluid carrier, but not substantially incorporated into the matrix of the porous substrate such that the porous substrate remains largely intact.

As used herein, the phrase "electrically conductive" refers to a material that transports electrons with a low resistance such that the electrical resistance of the material will not render it unfit for use in the desired application. In practice, this phrase typically means a resistivity lower than about $1 \times 10^{-3}$ ohm×cm.

As used herein, the phrases "electrically non-conductive material" and "electrically insulating material" refer to a material with a high resistance such that the electrical conductance of the material will not render it unfit for use in the desired application. In practice, these phrases typically mean a resistivity higher than about $1\times10^8$ ohm×cm.

DETAILED DESCRIPTION

Composite Material

Referring first to FIG. 1, an embodiment of a composite material 200 is shown including a porous polymer substrate 210 having a metallic region 220. The metallic region 220 may span a partial thickness of the porous polymer substrate 210, as shown in FIG. 1, or the entire thickness of the porous polymer substrate 210. The metallic region 220 may also extend beyond the thickness of the porous polymer substrate 210 into other layers. The metallic region 220 includes a nanoporous metal 224 present within the porous polymer substrate 210. As discussed further below, the metallic region 220 may provide electrical conductivity through the composite material 200.

The composite material 200 may be used for a wide range of applications, including but not limited to electrochemical analyte biosensors. As described herein and demonstrated in the Examples, the composite material 200 may have certain benefits over traditional nanoporous metals. First, the porous polymer substrate 210 may support or reinforce the nanoporous metal 224 to enhance its mechanical properties without a traditional carrier film. Also, the porous polymer substrate 210 may serve as a scaffold to facilitate an additive manufacturing process. Further, the porous polymer substrate 210 may have a controllable and larger average pore size than the nanoporous metal 224, such that the nanopores of the nanoporous metal 224 substantially fit inside the pores of the polymer substrate 210. These benefits may also support broader uses of the composite material 200.

The composite material 200 may comprise one or more hierarchical features. For example, the composite material 200 may have an interface region 217 distinct from the metallic region 220 to protect the metallic region 220 and enable bio-interface tailoring. In certain embodiments, the interface region 217 may be a unitary, integral, non-laminated portion of the porous polymer substrate 210. As another example, the composite material 200 may have gaps 226 between the nanoporous metal 224 and the porous polymer substrate 210 to promote tissue ingrowth and/or mass transport while maintaining electrical conductivity of the metallic region 220. As yet another example, the metallic region 220 of the composite material 200 may have pore size distribution including small and large nanopores. Without wishing to be bound by theory, this mixture of pore sizes may balance surface area and mass transfer of the composite material 200. These hierarchical features are described further below.

The composite material 200 may have a porosity of at least 30 vol. %, 40 vol. %, 50 vol. %, 60 vol. %, 70 vol. %, 80 vol. %, or more. The polymer of the polymer substrate 210 may account for less than 30 vol. %, 20 vol. %, or 10 vol. % of the composite material 200. The metal of the metallic region 220 may account for less than 40 vol. %, 30 vol. %, 20 vol. %, or 10 vol. % of the composite material 200. Despite its high porosity and low metal content, the composite material 200 may have good electrical conductivity.

Each element of the composite material 200 will now be described further below.

Porous Polymer Substrate

The porous polymer substrate 210 of the composite material 200 may be a biocompatible, flexible, chemically inert material. In certain embodiments, the porous polymer substrate 210 may comprise a fluoropolymer such as expanded polytetrafluoroethylene (ePTFE), a polyolefin such as expanded polyethylene (ePE), or another suitable polymer. The flexibility (or bending stiffness) of the porous polymer substrate 210 can be measured using, for example, a Kawabata Pure Bending Tester.

As shown in FIG. 1, the porous polymer substrate 210 has a first (i.e., upper in FIG. 1) surface 212, a second (i.e., lower in FIG. 1) surface 214, and a plurality of interconnected pores 216 between the first and second surfaces 212, 214. The porous polymer substrate 210 may also include one or more interface regions 217 at the first and/or second surfaces 212, 214. The interface region 217 may be distinct from the metallic region 220 and may not contain electrically conductive material (e.g., may be unmetallized or otherwise bare). In certain applications in which the composite material 200 is associated with a living organism, the interface regions 217 may serve as tissue interface regions that support integration and/or ingrowth of tissue T (illustratively, capillaries) through the first and/or second surfaces 212, 214 and into the pores 216. Such integration and/or ingrowth of tissue T may increase the biocompatibility of the composite material 200 and minimize deleterious reactions in surrounding tissue such as fibrous encapsulation or chronic inflammation. It is also within the scope of the present disclosure for the interface region 217 to include one or more bioactive agents to promote such integration and/or ingrowth of tissue T. Said therapeutic agents may be physically bound, covalently bound, physisorbed, or chemisorbed to the interface region 217 by means known to the art. In other applications, the interface region 217 may serve as a protective layer that protects the metallic region 220 from damage (e.g., abrasion) or fouling. The interface region 217 may be an integral, non-laminated portion of the porous polymer substrate 210.

The porous polymer substrate 210 may have a microstructure of nodes 218 with interconnecting fibrils 219 that cooperate to define the pores 216, which may comprise micropores as defined above. It is also within the scope of the present disclosure for the porous polymer substrate 210 to have a "nodeless" microstructure of interconnecting fibrils 219 that cooperate to define the pores 216. The fibrils 219 may vary in length from about 0.1 μm to about 1000 μm and in diameter from about 0.002 μm to about 100 μm, although these dimensions may vary. The porous polymer substrate 210 may have a characteristic or nominal pore size measured using techniques known in the art, such as the Bubble Point test method set forth below. Such techniques may be based on the ability of the porous polymer substrate 210 to filter particles of a particular size or resist fluid flow, not necessarily the size or shape of the pores 216 themselves.

In certain embodiments, the porous polymer substrate 210 may include a combination of both smaller pores 216 and larger pores 216. The larger pores 216 may be positioned outward near the first and/or second surfaces 212, 214 to encourage integration and/or ingrowth of tissue T, while the smaller pores 216 may be positioned inward near the center of the porous polymer substrate 210, which may be adjacent to the metallic region 220.

The porous polymer substrate 210 itself may be hydrophobic or hydrophilic. In hydrophilic embodiments, the porous polymer substrate 210 may have a tendency to mix with or be wetted by water or other polar fluids, including polar biological fluids such as blood.

The porous polymer substrate 210 may be shaped and sized to arrive at the desired shape and size of the composite material 200. For example, the porous polymer substrate 210 may be shaped as a membrane, film, fiber, tube, or another desired shape to produce a similarly shaped composite material 200. The porous polymer substrate 210 may also be buckled, micro-wrinkled, stretched, rolled, folded, cut, or otherwise physically manipulated to arrive at the desired shape and compliance of the composite material 200 based on the surrounding environment. In certain embodiments, it may be desirable for the compliance of the porous polymer substrate 210 to match or approach the compliance of surrounding tissue.

Metallic Region

The metallic region 220 comprises the nanoporous metal 224 contained at least partially within the interconnected pores 216 of the porous polymer substrate 210 without being substantially incorporated into the matrix of the porous polymer substrate 210. In this arrangement, the nodes 218 and the fibrils 219 of the porous polymer substrate 210 define a first continuous polymeric network, and the metallic region 220 may define a second substantially continuous, electrically conductive metallic network that interpenetrates the polymeric network. In this way, the polymeric network of the porous polymer substrate 210 and the metallic network of the metallic region 220 may be substantially co-continuous and interpenetrating, at least within the metallic region 220. In one example, the nanoporous metal 224 is a nanoporous gold (NPG). In other non-limiting examples, the nanoporous metal 224 is platinum, iridium, palladium, silver, copper, nickel, or a combination or an alloy thereof.

The metallic network may comprise hierarchical features. For example, unlike a conformal coating, the nanoporous metal 224 may be spaced apart from and avoid substantial contact with the porous polymer substrate 210, especially the nodes 218 of the porous polymer substrate 210. These gaps 226 between the nanoporous metal 224 and the nodes 218 may be micropores that promote tissue ingrowth and/or mass transport through the porous polymer substrate 210 without disrupting the metallic network of the metallic region 220 and while also maintaining mechanical reinforcement from the porous polymer substrate 210. These gaps 226 may be exposed at the surface of the composite material 200 (e.g., in the thickness or z-direction of FIG. 3B) to enable such tissue ingrowth while maintaining electrical conductivity (e.g., in at least the in-plane or x-y direction of FIG. 3B).

In another example of a hierarchical feature, the nanoporous metal 224 of the present disclosure may comprise a unimodal and right-skewed number-based nanopore size distribution in certain embodiments. In some typical preparations of nanoporous metals known in the art, the number-based nanopore size distribution is unimodal and monodisperse, or in other words, the mean nanopore size is approximately the mode nanopore size (for example A Pastre, "Porous Gold Films Fabricated by Wet-Chemistry Processes", J Nanomater, vol 2016, article ID 3536153, 2016). In other typical preparations of nanoporous metals known in the art, the nanopore size distribution is multimodal and complex, in other words, more than one mode nanopore size are present (for example, Y. Ding, "Nanoporous Metals with Controlled Multimodal Pore Size Distribution", J Am Chem Soc, vol 125, p 7772, 2003). In embodiments of the instant invention, however, the number-based nanopore size distribution of the nanoporous metal 224 is unimodal and right-skewed, in other words, the mean number-based nanopore size is substantially larger than (e.g., at least 75%, 100%, 125%, 150%, 175%, 200%, 225%, or 250% larger than) the single mode number-based nanopore size, indicating that a large number of nanopores are greater than the single mode and only a small number of nanopores are smaller than the single mode (See FIG. 5 and Examples 1 and 14 below). The unimodal and right-skewed number-based nanopore size distribution of the nanoporous metal 224 may provide benefits in terms of performance in challenging environments, such as in a high surface-tension fluid environment, a biofouling environment, or a tissue integration environment. For example, the nanopore size distribution may balance surface area and mass transfer throughout the composite material 200.

The right-skewed number-based nanopore size distribution may be characterized by the average pore size being substantially larger than (e.g., at least 10%, 20%, 30%, 40%, 50%, 60%, or 70% larger than) the median pore size.

The nanoporous metal 224 of the present invention may comprise a volume-based pore size distribution for which the mode is substantially larger than (e.g., at least 200%, 500%, 1000%, 1500%, 2000%, 2500%, 3000%, 3500%, or 4000% larger than) the mode of the number-based pore-size distribution.

The nanoporous metal 224 of the present invention may comprise a volume-based pore size distribution for which the average is substantially larger than (e.g., at least 150%, 200%, 250%, 300%, 350%, 400%, 450%, 500%, 550%, or 600% larger than) the average of the number-based pore-size distribution.

An imbibing process may be performed to load the porous polymer substrate 210 with the nanoporous metal 224. This process may involve: (1) producing a non-aqueous wetting solution including a metallic precursor (e.g., salt) in a non-aqueous solvent, (2) imbibing the porous polymer substrate 210 with the non-aqueous wetting solution, and (3) heating the imbibed construct to remove elements of the non-aqueous wetting solution, reduce the metallic precursor to the metallic state, sinter the metal, and leave behind the nanoporous metal 224. The non-aqueous wetting solution may be tailored to thoroughly wet the porous polymer substrate 210. In the case of a hydrophobic, ePTFE porous polymer substrate 210, for example, the non-aqueous wetting solution may include a wetting package of a substantially water-insoluble alcohol and a surfactant, in accordance with the teachings of U.S. Pat. No. 9,018,264. The heating step may involve heating the construct at one or more temperatures up to about 300° C. or more for a suitable time up to several hours. In certain embodiments, the imbibing process may be controlled such that the nanoporous metal 224 is loaded into the porous polymer substrate 210 in a desired pattern. This desired pattern may be achieved by controlling delivery of the metallic precursor into the porous polymer substrate 210, similar to ink-jet printing or other means of printing or lithography known in the art, by masking certain areas of the porous polymer substrate 210, or by other suitable techniques.

Application as Working Electrode of Electrochemical Analyte Biosensor

One potential application of the composite material 200 is as a working electrode of an electrochemical analyte biosensor, which transduces interactions between a bioreceptor (e.g., enzymes, aptamers, exosomes, catalytic antibodies, catalytic ribonucleic acids, catalytic polysaccharides, and the like) and an analyte (e.g., glucose, lactate, pyruvate, glycerol, glutamate, glutamine, peptides, hormones, heart-specific enzymes, opioids/narcotics, and chemotherapeutic agents) to an electrical signal at least in part via an electrochemical process to produce a signal containing information about the analyte, for example its concentration. The composite material 200 may further include one or more diffusion barrier regions and one or more immobilized bioreceptor regions. In use, the nanoporous metal 224 of the metallic region 220 may provide electrical conductivity through and along its surface. Thus, the metallic region 220 may be capable of detecting a target analyte and transmitting corresponding electrical signals to an electronic processor (not shown). Additional details regarding use of the composite material 200 in the electrochemical analyte biosensor application are disclosed in the co-pending U.S. Application No. 63/176,653 (Applicant Ref. 1862US01), which was filed on the same date as the present application.

The nanoporous metal 224 of the present disclosure may exhibit a steady electrochemical surface area regardless of the surface tension of a surrounding biological fluid. It is known to the art that, for full functionality of an implanted biosensor, an electrode's entire surface and microstructure must be contacted or wetted by the biological fluid to enable the entire electrode surface area to be active for analyte sensing. The fluid's ability to wet the microstructure is related to its surface tension, such that fluids having high surface tensions (greater than about 50 mN/m), such as saline (about 72 mN/m) and blood (about 50 mN/m) have a lower tendency to wet hydrophobic substrates. In contrast, fluids having low surface tensions (lower than about 30 mN/m), such as isopropanol (about 23 mN/m) and a 50:50 saline:isopropanol mixture (about 25 mN/m) have a higher tendency to wet hydrophobic substrates. Because the composite material 200 of the present disclosure may comprise a hydrophobic porous polymer substrate 210 such as ePTFE, it would be expected that contact or wetting by a high surface-tension biological fluid would be reduced, which would also reduce the electrochemical surface area and/or analyte sensing activity of the metallic region 220. The presence of the imbibed nanoporous metal 224 within the pores 216 of the hydrophobic porous polymer substrate 210 would not be expected to change the hydrophobic nature of the composite material 200, because the hydrophobic porous polymer substrate 210 is present in excess, including along the first and second surfaces 212, 214. In other words, it would be expected that the composite material 200 comprising the hydrophobic porous polymer substrate 210 imbibed with the nanoporous metal 224 would itself be hydrophobic, and therefore contact or wetting by a high surface-tension biological fluid would be reduced. However, the present inventors surprisingly discovered that the electrochemical surface area of the composite material 200 with the imbibed nanoporous metal 224 was not strongly dependent on wetting by the fluid's surface tension, thus permitting the composite material 200 to function in low or high surface-tension biological fluids. For example, the electrochemical surface area of the composite material 200 with the imbibed nanoporous metal 224 may change by about 50% or less, about 25% or less, or about 10% or less between low and high surface-tension biological fluids (See FIG. 12 and Example 10 below). This unexpected wetting behavior may be utilized to exploit the high surface area of the imbibed nanoporous metal 224.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale but may be exaggerated to illustrate various aspects of the present disclosure, and in that regard, the drawing figures should not be construed as limiting.

Test Methods

It should be understood that although certain methods and equipment are described below, other methods or equipment determined suitable by one of ordinary skill in the art may be alternatively utilized.

Non-Contact Thickness

Non-contact thickness was measured using a laser micrometer (Keyence Model No. LS-7010, Mechelen, Belgium) using the following technique. A metal cylinder was aligned between the laser micrometer source and the laser micrometer receiver such that a first shadow of the top of the cylinder was projected onto the receiver. The position of the first shadow was then set as the "zero" reading of the laser micrometer. A single layer of test article was then draped over the surface of the metal cylinder without overlap and without wrinkles, which projected a second shadow onto the receiver. The laser micrometer then indicated the change in the position between the first and the second shadows as the thickness of the sample. Each thickness was measured three times and averaged for each sample.

Mass Per Area

The mass per area of samples was measured according to standard ASTM D 3776 (Standard Test Methods for Mass Per Unit Area (Weight) of Fabric, test method Option C).

Bubble Point

Bubble point pressures were measured according to ASTM F31 6-03 using a Capillary Flow Porometer (Model 3Gzh from Quantachrome Instruments, Boynton Beach, Florida), and using Silwick Silicone Fluid (20.1 dyne/cm; Porous Materials Inc.). The values presented for bubble point pressure are the average of two measurements.

Sheet Resistance

Figure 2:
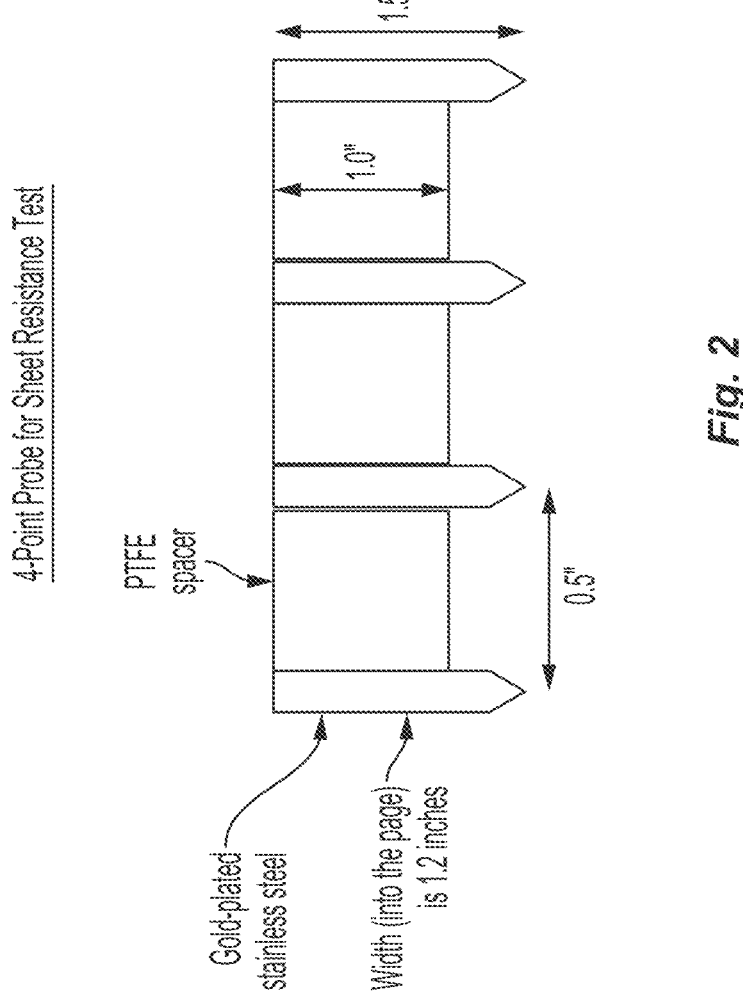
FIG. 2 is a schematic view of an apparatus used to measure a sample's sheet resistance.

A 2.125"×0.5" sample was die cut from the sheet of material to be tested. The sample was placed flat on a closed cell silicone sponge sheet (½ inch thick, Bellofoam #7704). The resistance was measured with a Keithley 2750 Digital Multimeter, utilizing a 4-point probe as shown in FIG. 2. The 4-point probe was connected to the Multimeter in the standard 4-point probe configuration (i.e., with the voltage sense leads on the two innermost terminals and the input leads on the two outermost terminals). After gently placing the 4-point probe on the sample to be measured, a 330-gram weight was placed on top of the probe to ensure the probe made reliable, uniform contact with the sample. Care was taken to ensure adequate contact between the probe and the conductive phase of the sample. The weight was insulated with a plastic sheet to ensure it did not short-circuit the probe. The Keithley Multimeter was operated in 4-point probe mode with "OCOMP" 4-wire offset compensation enabled. For each measurement, the system was allowed to stabilize for approximately 10 seconds before the resistance value was recorded. The data are reported in units of ohms per square area.

Quantitative Image Analysis to Measure Pore Size within the Metal Phase

To collect an image for pore size analysis, a cross-section of each sample was prepared with a broad beam ion mill (Illon 2, Gatan, United States) to preserve its structure. A sputter coater (208HR, Cressington, England) was used to apply a thin conductive platinum coating to improve sample stability under the electron beam during SEM imaging. A cross-sectional image of the structure was taken at 50,000× magnification (2.5 µm horizontal field width) with scanning electron microscopy (SEM: SU8200, Hitachi, Japan) at a resolution of at least 2560 pixels×1920 pixels.

Analysis of the pore size within the metal phase was carried out via quantitative analysis of the cross-sectional SEM images with "Fiji" ImageJ 1.53 software. The automated macros set forth in Table 1 below were used to minimize subjectivity and maximize reproducibility of the data analyses.

TABLE 1

```
Macro1_PreProcess
  / Gets the File Directory and Name for the open image
  Directory = getDirectory ("image")
  FileName = getTitle( );
  // Ensures the Image Type is 8-bit grayscale
  run("8-bit");
  // Creates Dialog box for user to input Magnification value
  title = "Input Image Magnification for Scale";
  Dialog.create("New Image");
  Dialog.addString("Magnification:", "50k");
  Dialog.addMessage( "General Formatting: \n 50k OR 50.00k OR 50,000 OR
  50000" );
  Dialog.show( );
  // Interprets Magnification value into image's Pixels/Micron resolution
  mag = parseFloat( replace( replace( replace( Dialog.getString( ) , "k" , "000" )
  , "." , "" ) , "," , "" ) );
  MAG = d2s( mag*0.02016 , 1 );
  run("Set Scale...", "distance="+MAG+" known=1 pixel=1 unit=um");
  // Crops out the SEM description & Saves "crop" file
  makeRectangle(0, 0, 2560, 1770);
  run("Crop");
  NameCropped = replace( Directory+FileName , ".tif" , "_crop.tif" );
  saveAs("Tiff", NameCropped );
  // Applies "auto" Non-Local Means Denoising plugin & Saves "0" file
  run("Non-local Means Denoising", "sigma=15 smoothing_factor=1 auto");
  NameNLMD = replace( Directory+FileName , ".tif" , "_0.tif" );
  saveAs("Tiff", NameNLMD );
  // Alerts user to verify that Macro worked - no checks are programmed!!
  close( );
  open( NameCropped );
  open( NameNLMD );
  print("Please confirm both images saved w/ reasonable scale.");
  // Sets appropriate Color for future deletions
  run("Color Picker...");
  setBackgroundColor(255, 255, 255);
  setForegroundColor(0, 0, 0);
  run("Close");
Macro2_After_Segmenting_Support
  // Gets the File Directory and Name for the open image
  Directory = getDirectory("image")
  FileName = getTitle( );
  NamePTFE = replace( FileName , "_0.tif" , "_PTFE-Mask.tif" );
  NameCrop = replace( FileName , "_0.tif" , "_crop.tif" );
  // Ensures the Image Type is 8-bit grayscale
  run("8-bit");
  run("Select None");
  // Create Mask
  setThreshold(255, 255);
  setOption("BlackBackground", false);
  run("Convert to Mask");
  run("Close-");
  run("Select None");
  saveAs("Tiff", Directory+NamePTFE );
  run("Select None");
  open( Directory+NameCrop );
  run("Select None");
  selectWindow( NamePTFE );
  run("Create Selection");
  selectWindow( NameCrop );
  run("Restore Selection");
  run("Clear", "slice");
  run("Select None");
  selectWindow( NamePTFE );
  run("Close");
  print("PTFE selected. Now select Void space and add it to the white
  section.");
Macro3_After_Segmenting_Void
  // Gets the File Directory and Name for the open image
  Directory = getDirectory("image")
  FileName = getTitle( );
  // Ensures the Image Type is 8-bit grayscale
  run("8-bit");
```

TABLE 1-continued

```
// Create Mask
setThreshold(255, 255);
setOption("BlackBackground", false);
run("Convert to Mask");
run("Invert");
run("Close-");
run("Select None");
// Saves resultant Gold mask
NameGold = replace( FileName , "_crop.tif" , "_Gold-Mask.tif" );
saveAs("Tiff", Directory+NameGold );
run("Invert");
run("Create Selection");
// Creates output Image of Gold Only
NameNLMD = replace( FileName , "_crop.tif" , "_0.tif" );
open( Directory+NameNLMD );
run("Restore Selection");
setBackgroundColor(0, 0, 0);
run("Clear", "slice");
run("Select None");
setBackgroundColor(255, 255, 255);
NameGoldOnly = replace( FileName , "_crop.tif" , "_0Gold.tif" );
saveAs("Tiff", Directory+NameGoldOnly );
NamePTFE = replace( FileName , "_crop.tif" , "_PTFE-Mask.tif" );
open( Directory+NamePTFE );
run("Create Selection");
selectWindow( NameGold );
run("Restore Selection");
run("Clear", "slice");
run("Select None");
selectWindow( NamePTFE );
run("Select None");
run("Close");
NameVoid = replace( FileName , "_crop.tif" , "_Void-Mask.tif" );
saveAs("Tiff", Directory+NameVoid );
run("Select None");
run("Close");
print("All 3 Segmentation Masks are created.");
Macro4_Analysis
  / Gets the File Directory and Name for the open image
  Directory = getDirectory("image")
  FileName = getTitle( );
  selectWindow(FileName);
  title = "Estimate 3-Sigma Threshold";
  Dialog.create("New Image");
  Dialog.addString("Value at Left of Peak", "100");
  Dialog.addMessage( "Representing approximately 2-4 standard deviations
  below the max" );
  Dialog.show( );
  Sigma = d2s( parseFloat( replace( Dialog.getString( ) , " " , "" )) , 0 );
  selectWindow(FileName);
  run("Find Connected Regions", "allow_diagonal display_one_image
  autosubtract regions_for_values_over="+Sigma+"
  minimum_number_of_points=20 stop_after=-1");
  selectWindow("All connected regions");
  setThreshold(1, 65535); run("Convert to Mask");
  run("Close-"); run("Open");
  saveAs("Tiff", Directory+replace( FileName , "tif" , "-InPlane.tif" ) );
  close( );
  selectWindow(FileName);
  setThreshold(1, 255); run("Convert to Mask");
  run("Close-"); run("Open");
  saveAs("Tiff", Directory+replace( FileName , ".tif" , "-InPlane-PoreSpace.tif" )
  );
  close( );
  // Overlay "GOLD" onto crop image
  open(Directory+replace( FileName , ".tif" , "-InPlane.tif" ));
  run("Create Selection");
  open(Directory+replace( FileName , "_0Gold.tif" , "_Crop.tif" ));
  run("Restore Selection");
  run("RGB Color"); setForegroundColor(255, 201, 0); run("Fill", "slice");
  run("Select None");
  selectWindow( replace( FileName , ".tif" , "-InPlane.tif" ) );
  close( );
  // Overlay "PTFE" onto crop image
  open(Directory+replace( FileName , "_0Gold.tif" , "_PTFE-Mask.tif" ));
  run("Create Selection");
  selectWindow(replace( FileName , "_0Gold.tif" , "_Crop.tif" ));
  run("Restore Selection");
  setForegroundColor(185, 0, 255);
  run("Fill", "slice");
```

TABLE 1-continued

```
run("Select None");
saveAs("Tiff", replace( FileName , "__0Gold.tif" , "__Highlight. tif" ));
//
open(Directory +replace( FileName , "__0Gold. tif" , "__Crop.tif" ));
selectWindow(replace( FileName , "__0Gold.tif" , "__Highlight.tif" ));
run("Add Image...", "image="+replace( FileName , "__0Gold.tif" , "__Crop.tif"
)+" x=0 y=0 opacity=70");
run("Flatten");
saveAs("Tiff", Directory+replace( FileName , "__0Gold.tif" , "__In-
Plane__Highlight.tif" ));
//
open( Directory+replace( FileName , ".tif" , "-InPlane-PoreSpace.tif" ) );
run("Set Measurements...", "area centroid center perimeter bounding fit
shape feret's area__fraction redirect=None decimal=3");
run("Analyze Particles...", "size=20-Infinity pixel show=Overlay display");
saveAs("Results", Directory+replace( FileName , ".tif" , "-InPlane-
PoreSpace.csv" ));
close("*");
// Evaluating Pore Structure...
open(Directory+replace( FileName , ".tif" , "-InPlane-PoreSpace.tif" ));
run("Create Selection");
open(Directory+replace( FileName , "__0Gold.tif" , "__Crop.tif" ));
run("Restore Selection");
run("RGB Color");
setForegroundColor(255, 0, 182);
run("Fill", "slice");
run("Select None");
saveAs("Tiff", Directory+replace( FileName , "__0Gold.tif" , "__Pore-
Highlight.tif" ));
open(Directory+replace( FileName , "__0Gold.tif" , "__Crop.tif" ));
selectWindow(replace( FileName , "__0Gold.tif" , "__Pore-Highlight.tif" ));
run("Add Image...", "image="+replace( FileName , "__0Gold.tif" , "__Crop.tif"
)+" x=0 y=0 opacity=70");
selectWindow(replace( FileName , "__0Gold.tif" , "__Crop.tif" ));close( );
run("Flatten");
saveAs("Tiff", Directory+replace( FileName , "__0Gold.tif" , "__Pore-
Highlight.tif" ));
close("*");
open(Directory+replace( FileName , "__0Gold.tif" , "__Pore-Highlight. tif" ));
```

First, the cross-sectional SEM image was pre-processed using the "Macro1_PreProcess" macro of Table 1 above to remove gray scale fluctuations caused by the conductive Pt coating.

Next, the pre-processed image was manually censored to eliminate all regions except those constituting the metal phase and its embedded porosity that are in the plane of the cross-section. Manual censoring comprised identifying visual cues such as surface texture and perspective. The manual censoring was performed with the assistance of the "Macro2_After_Segmenting_Support" and "Macro3_After_Segmenting_Void" macros of Table 1 above.

Finally, the pre-processed and manually censored image was analyzed using the "Macro4_Analysis" macro of Table 1 above. This macro parsed the image to identify individual pores, which comprised sub-dividing the complex pore space into individual pores separated by throats. This macro also produced a data file tabulating a variety of measurements for each individual pore according to the ImageJ documentation accessible at https://imagej.nih.gov/ij/docs/menus/analyze.html #set as of Jun. 29, 2020. In particular, the data file included the pore size measurements set forth in Table 2 below.

TABLE 2

| Measurement | Description |
| --- | --- |
| Fit Ellipse | Fit an ellipse to the selection. Uses the headings Major, Minor and Angle. Major and Minor are the primary and secondary axis of the best fitting ellipse. Angle (0-180 degrees) is the angle between the primary axis and a line parallel to the x-axis of the image. The coordinates of the center of the ellipse are displayed as X and Y if Centroid is checked. Note that ImageJ cannot calculate the major and minor axis lengths if Pixel Aspect Ratio in the Set Scale dialog is not 1.0. |

TABLE 2-continued

| Measurement | Description |
| --- | --- |
| Feret's Diameter | The longest distance between any two points along the selection boundary, also known as maximum caliper. Uses the Feret heading. FeretAngle (0-180 degrees) is the angle between the Feret's diameter and a line parallel to the x-axis of the image. MinFeret is the minimum caliper diameter. The starting coordinates of the Feret's diameter (FeretX and FeretY) are also displayed. The DrawFeretDiameter macro draws the Feret's diameter of the current selection. |

The pore size of an individual pore was defined as the average of the major and minor axes of the best-fit ellipse. To depict the pore size distribution, the pore sizes of all pores in the data table were plotted as a histogram. A quality check was also performed to ensure that the pores had been parsed correctly. This quality check ensures that the pores have not been under-parsed (meaning that multiple connected pores have been defined as a single pore) or over-parsed (meaning that a single pore has been sub-divided into multiple pores). The ratios of "major axis to the feret's diameter" and "minor axis to the minferet" were checked to ensure they were within the range of 0.5-1.2; such a range is close to unity, and confirms data are quality-checked. In this manner, a processed image was produced for pore size analysis.

To determine the pore size distribution on a number basis, a histogram was generated by the following means. The pores were bucketed in groups that were 3 nm wide between 0 nm and 1500 nm (i.e., the first group included all pores >0 nm and <=3 nm, the second group included all pores >3 nm and <=6 nm, and so on until the final group, which included all pores >1497 nm and <=1500 nm). The "pore size" of each group was the average of the pore size range rounded down to the nearest micron (i.e., the pore size of the first group was 1 nm, the pore size of the second group was 4 nm, and so on until the final group, the size of which was 1498 nm). The frequency of pores in each group was determined by dividing the number of pores in that group by the total number of pores. To plot the pore size distribution on a number basis, the frequency of pores of each group was assigned to the y-axis, and the pore size of the group was assigned to the x-axis.

The pore size distribution on a number basis was then used to calculate the pore size distribution on a volume basis. To calculate the unit pore volume of each group, the number-based frequency of pores in each group was multiplied by the "pore size" of the group raised to the third power. To calculate the pore volume % of each group, the unit pore volume of each group was divided by the sum of the unit pore volumes over all groups. To plot the pore size distribution on a volume basis, the pore volume % of each group was assigned to the y-axis, and the pore size of the group was assigned to the x-axis.

The number-weighted average pore size was calculated by weighting the pore size of each group by the numerical frequency. The volume-weighted average pore size was calculated by weighting the pore size of each group by the volume %. The mode of each distribution was determined by taking the maximum value of the peak in the distribution.

To elaborate further upon the quantitative image analysis test method, the principles behind the design of this test method are described in more general terms. To satisfy this test method, a cross-sectional SEM image is taken that is representative of the pore phase, the portion of the image that shows nanoporous metal in the plane of the cross-section is isolated, and the sizes of those pores are quantified. The visual cues required to remove image artifacts and isolate the proper portion of the image for analysis, including texture and perspective, referred to above as "censoring", are readily apparent to one of ordinary skill in the art. The pore phase parsed for analysis should demonstrate excellent fidelity to the SEM image when the two are visually compared (See, for example, FIGS. 7A-7C). The minimum feature size that can be resolved corresponds to about 5 pixels. The use of the diameter-to-feret ratios provide a practical check to ensure that parsing of pores to determine their individual sizes is done correctly.

Glucose Amperometric Benchtop Test

An amperometric benchtop test was conducted using the following system. A finished electrode (comprising a diameter of 4 mm) was immersed into a 20 ml beaker containing phosphate buffered saline (PBS) and a magnetic stir bar, alongside a Ag/AgCl reference electrode (Gamry), and alongside a 0.25 mm platinum wire counter electrode (Alfa Aesar) connected to a potentiostat system (Digi-Ivy #DY211, or Gamry Reference 600) with a set potential of 0.6 to 0.7 V and an oversampling rate of 5 Hz. Working electrode voltages are reported versus the reference (or pseudo-reference) electrode. The system was allowed to equilibrate for 60 min with magnetic stirring at 300 rpm. Varying microliter volumes of a test solution (D-(+)-glucose, 0.4 g/mL in deionized water) were pipetted to the PBS every 50 to 500 seconds to serially increase the concentration of glucose, and current was measured as a function of time.

Pseudo-Reference Electrode Test

To perform the test, a potentiostat (Gamry Reference 600) was used in conjunction with Gamry Instruments Echem Analyst Software and Gamry Instruments Framework™ Data Acquisition Software. Two variants of a three-electrode electrochemical cell were assembled. The electrolyte solution comprised 1 M potassium chloride (Sigma Aldrich) with 1 mM potassium ferricyanide (Sigma Aldrich), in deionized water (>18 M-Ohm).

The first variant (representing a variant traditionally used in the art) consisted of a liquid junction Ag/AgCl reference electrode (Gamry), a platinum wire (99.9%) as a counter electrode, a 3 mm diameter planar gold electrode (Alfa Aesar) as a working electrode, and the electrolyte solution. The working electrode and the reference electrode were physically separated by a distance of about 1 cm.

The second variant consisted of an ePTFE silver imbibed film as a pseudo-reference electrode, a platinum wire (99.9%) as a counter electrode, a NPG/ePTFE membrane (housed in a PTFE electrochemical cell with a 3 mm diameter opening) as a working electrode, and the electrolyte solution. The pseudo-reference electrode and the working electrode were physically separated by a distance of about 1 cm.

Cyclic voltammograms were generated on the variants, using an initial potential of 0.5 V versus the reference (or pseudo-reference) electrode, scanning to –0.1 V followed by a reverse scan to 0.5 V at a scan rate of 50 mV/s.

Biofouling Resistance Test

A biofouling test was developed to evaluate a sample electrode's electrochemical performance in the presence of common biofouling media such as bovine serum albumin (BSA). Unless otherwise specified, solutions are aqueous.

A potassium ferricyanide stock solution (2 mM in 0.1 M KCl solution) was employed as small molecule redox generator for characterizing electrochemical performance. A set of BSA biofouling test solutions was prepared by dissolving BSA in the potassium ferricyanide stock solution at 2 mg/mL, 6 mg/mL, 10 mg/mL, 15 mg/mL, and 25 mg/mL.

The sample electrode's surface was rinsed with 70% isopropanol for 3-5 seconds, and then the sample electrode was placed in a 20 ml beaker filled with 0.05 M sulfuric acid solution, alongside an Ag/AgCl reference electrode, and a 0.25 mm platinum wire counter electrode, connected to a potentiostat system (Digi-Ivy #DY211). Working electrode voltages are reported versus the reference (or pseudo-reference) electrode. A cleaning CV scan (10 cycles, scan range: 0 to 1.5 V, scan rate: 50 mV/s), was performed to clean the working electrode. After cleaning, the electrode was taken out of the sulfuric acid test cell and rinsed with DI water, and then Kimwipes® tissue was used to absorb residual water.

The sample electrode, the Ag/AgCl reference electrode, and the platinum wire counter electrode were immersed a 20 ml beaker filled with the potassium ferricyanide stock solution. A continuous CV scan (10-20 cycles, scan range: –0.2 to 0.6 V, scan rate: 100 mV/s), was performed to obtain baseline CV data. Then, the electrodes were moved to another 20 ml beaker filled with the BSA biofouling test solutions, followed a continuous CV scan (100 cycles, scan range: –0.2 to 0.6 V, scan rate: 100 mV/s), to obtain biofouling CV data. The peak currents from the potassium ferricyanide stock solution were compared with the peak currents from the BSA biofouling test solutions to evaluate the sample electrode's electrochemical performance in the presence of biofouling media.

Capillary Flow Porometry (CFP) Test

Measurements were made using a Quantachrome Porometer 3G zH. The wetting fluid was silicone oil with a nominal surface tension of 19.78 dyne/cm. The pressure range was 0.255 psig to 394 psig. The sample size was 10 mm in diameter. The ramp rate setting was "2×" resulting in a run time of approximately 28 minutes. Only data for "wet" curves were generated (i.e., no data for "dry" curves were collected). The maximum measurable flow was 10 liters/min.

Wet Flex Particulation Test

Figures 14, 15:
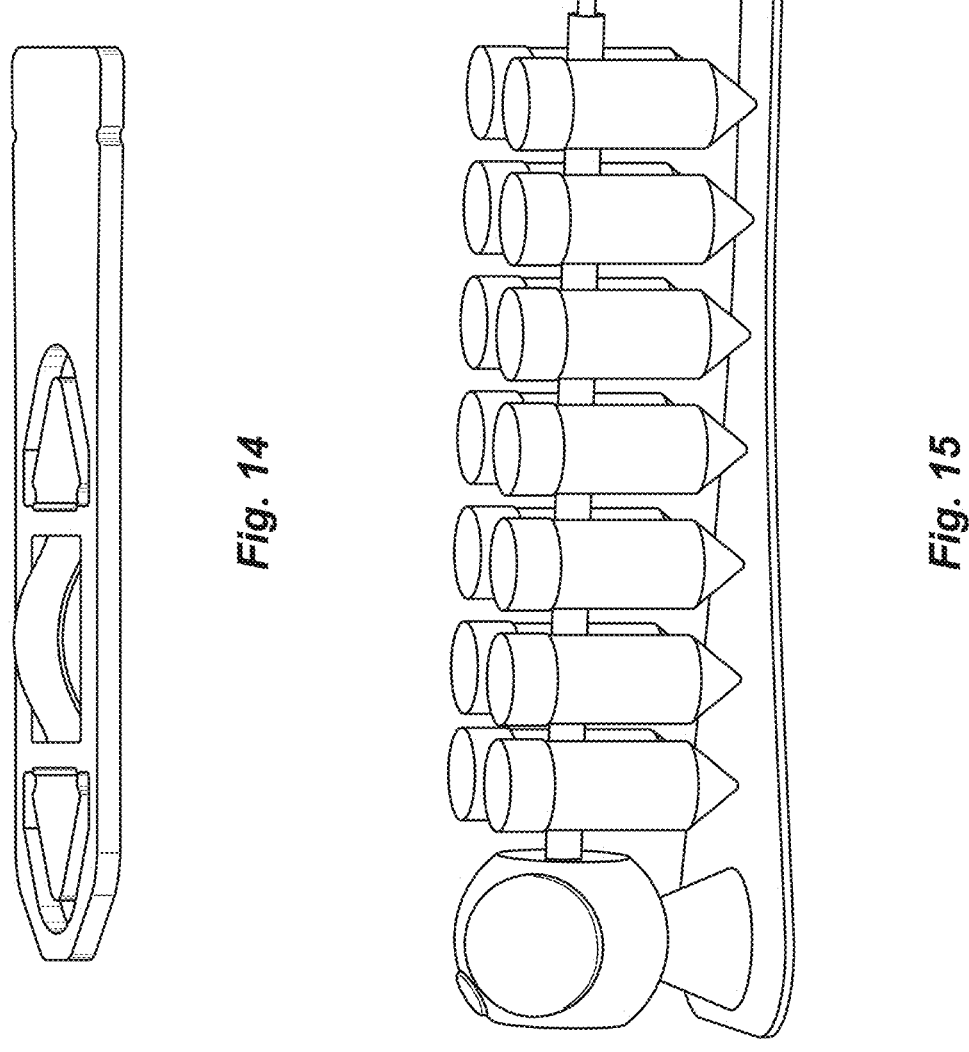

This durability test was developed to evaluate the tendency of the composite materials to shed particles. For the test to be effective, the samples must have sufficiently low bending stiffness to enable full flexural motion under the test conditions. To perform the test, a 2.125"×0.5" sample was cut from the composite material. The sample was loaded into a text fixture by sandwiching it between two pieces of engineering plastic cut to the shape shown in FIG. 13. The sample was loaded with a controlled amount of slack and held in place by o-rings as shown in FIG. 14. For scale, the size of the window that allows flexing of the sample is 24.5 mm long×14.1 mm wide×2.7 mm thick. The test fixtures containing the samples were then loaded into standard, 50 mL centrifuge tubes, which were then filled with isopropanol to the 40 mL line. The centrifuge tubes were then capped and taped closed to prevent leakage. As shown in FIG. 15, the centrifuge tubes were then loaded into an Intelli-Mixer (#RM-2 L) such that the plane of the test fixture was parallel to the axis of rotation. This orientation enables flexing of the sample. The Intelli-Mixer was set to rock the samples+/−99 degrees at 20 rpm for the desired time (typically 1-7 days). Each time the samples rocked, they also flexed due to the fluid dynamics inside the tube. Flexing means the slack in the sample switched from one side of the test fixture to the other. After rocking for the desired time, the liquid in the tube was extracted using a pipet and analyzed using ICP-MS to check for the presence of metal that may have been shed from the composite material.

Electrochemical Surface Area (ECSA) Test

Figure 17:
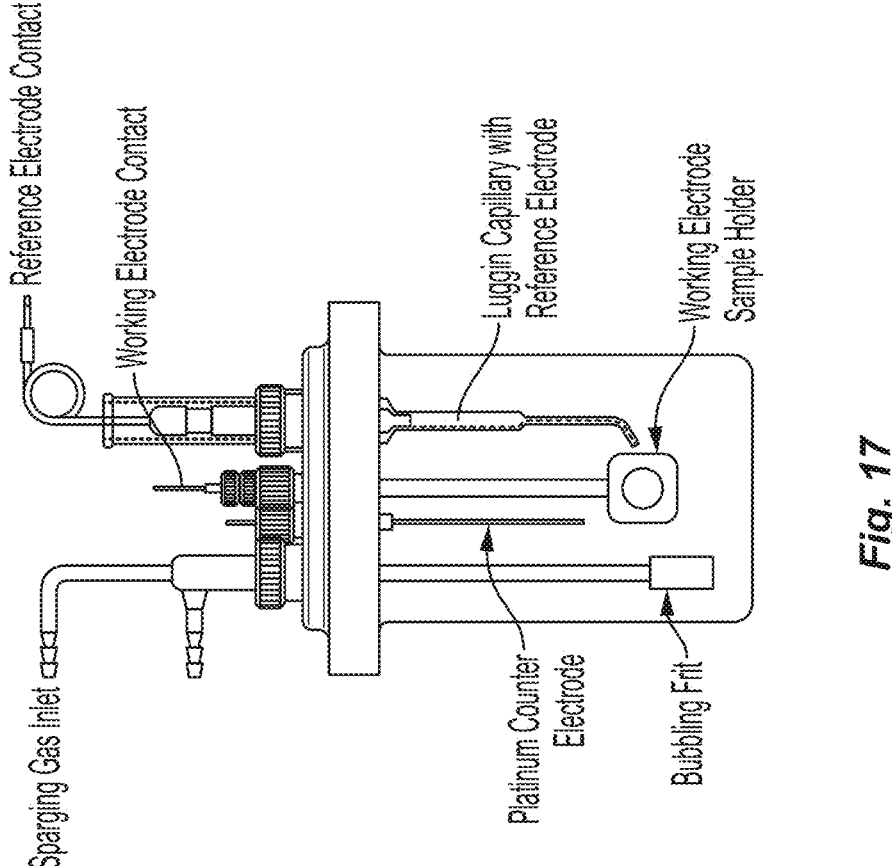
FIG. 17 is a schematic view of an electrochemical cell design for an electrochemical surface area (ECSA) test.

Electrochemical tests were carried out in a WonATech CCK05 Corrosion Cell Kit (500 mL), as shown in FIG. 17. Working electrode samples were held in a WonATech FSH2 Flat Specimen Holder of 11.28 mm electrode diameter (1 cm²). The counter electrode was either a WonATech PFL5 Platinum Plate electrode (5 cm² of active area) or a 10 cm platinum wire (1.5 mm diameter, ≥ 99.9% trace metals basis from Sigma Aldrich, 349399-3.8G). The reference electrode was a Gamry 932-00018, Ag/AgCl, filled with and stored in saturated KCl solution. The cell utilized a Luggin capillary tube to bring the reference electrode close to the working electrode surface. The cell was filled with 500 mL of sulfuric acid (LabChem LC256801, 0.05 M). The control sample for the working electrode was gold foil (Sigma Aldrich 326496-1.5 G thickness 0.127 mm, 99.99% trace metals basis or equivalent). Nitrogen gas was bubbled through a glass frit for at least 10 minutes to remove dissolved oxygen from the electrolyte (the nitrogen purge was turned off during the cyclic voltammetry measurements to avoid stirring the electrolyte).

Samples were cut or punched so that they were circular disks 15.5 mm to 22 mm in diameter, then they were loaded into the Flat Specimen Holder. Care was taken when loading the sample holder to dry all o-rings and internal parts to ensure there was no ionically conductive path around the sample. Samples were wetted out with isopropanol and then submerged in electrolyte to ensure complete wetting. Cyclic Voltammetery (CV) scans were used to ensure that the working electrode was clean, as will be understood by one of ordinary skill in the art.

Electrochemical Surface Area was determined by measuring the double layer capacitance, because ECSA is proportional to double layer capacitance. To determine the double layer capacitance, representative cyclic voltammetry curves were collected by scanning the potential (vs. reference electrode) from 0 mV to 100 mV at the following scan rates: 100 mV/s, 50 mV/s; 20 mV/s; and 10 mV/s. The height of the curves in amps (h) at 50 mV was determined and plotted vs the sweep rate in V/s. Double layer capacitance was determined from the slope of the best-fit line. To determine the roughness factor, which is the ratio of the electrochemical surface area to the geometric surface area, the double layer capacitance of the sample was normalized by the double layer capacitance of the smooth gold foil, which was assumed to have a roughness factor of 1. To calculate the metal specific surface area, the roughness factor of the sample was divided by the metal mass-per-area of the sample.

EXAMPLES

Example 1: Preparation of NPG/ePTFE Composite

This example describes the preparation of an ePTFE membrane incorporated with nanoporous gold ("NPG/ePTFE composite").

An ePTFE membrane (3-5 g/m$^2$ mass/area; 1.5 psi bubble point; 92 μm non-contact thickness; W. L. Gore & Associates) was restrained in a 4.5" diameter metal hoop and tensioned by hand to remove wrinkles. A reactive gold ink in a solvent (Part #LXPM-G2-1019, Liquid X, Inc.) was mixed with a substrate wetting package of 1.0 g of LXPM-G2-1019, 0.05 g Tergitol® TMN-10 (Dow, Inc.), and 0.03 g 1-hexanol in accordance with the teachings of U.S. Pat. No. 9,018,264. The mixture was pipetted onto the surface of the membrane and spread evenly using a disposable pipet bulb until it wet through the ePTFE (about 30 seconds). Excess ink was removed by wiping the surface of the ePTFE membrane with a Kimwipe® tissue. The sample was dried with a heat gun and heated in a standard convection oven at 155° C. for 20 minutes, and then at 300° C. for 1 hour, to reduce and sinter the gold phase, and to remove residual ink solvents, reducing agents, and residual substrate wetting package. The result was the NPG/ePTFE composite.

Figure 3A:
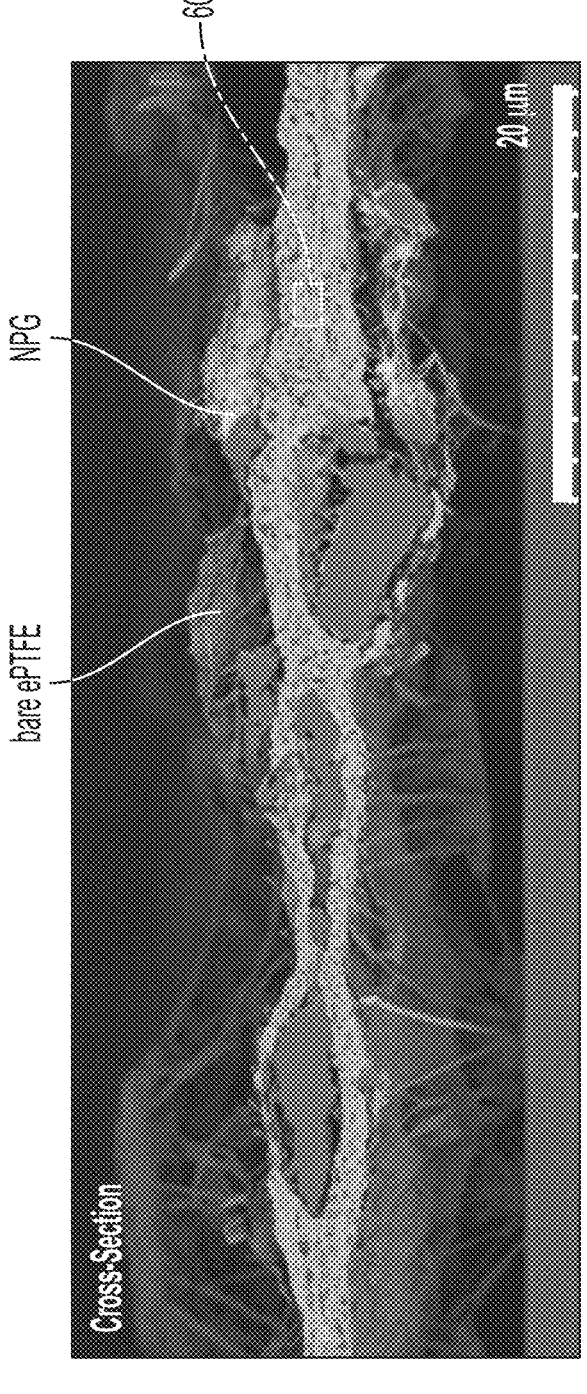
FIGS. 3A-3C are scanning electron micrograph (SEM) images showing the microarchitecture of the nanoporous gold (NPG)/expanded polytetrafluoroethylene (ePTFE) composite of Example 1.
Figure 3B:
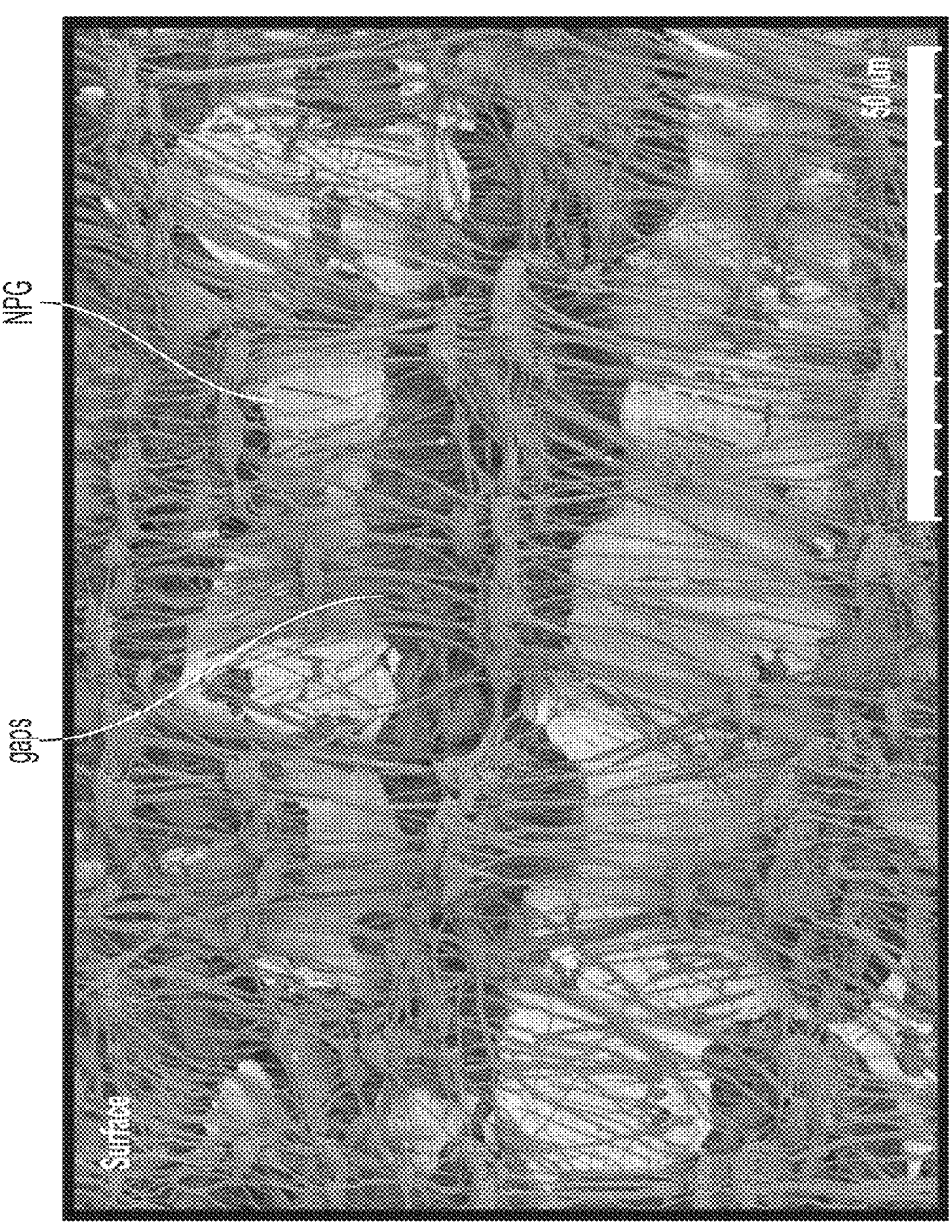
Figure 3C:
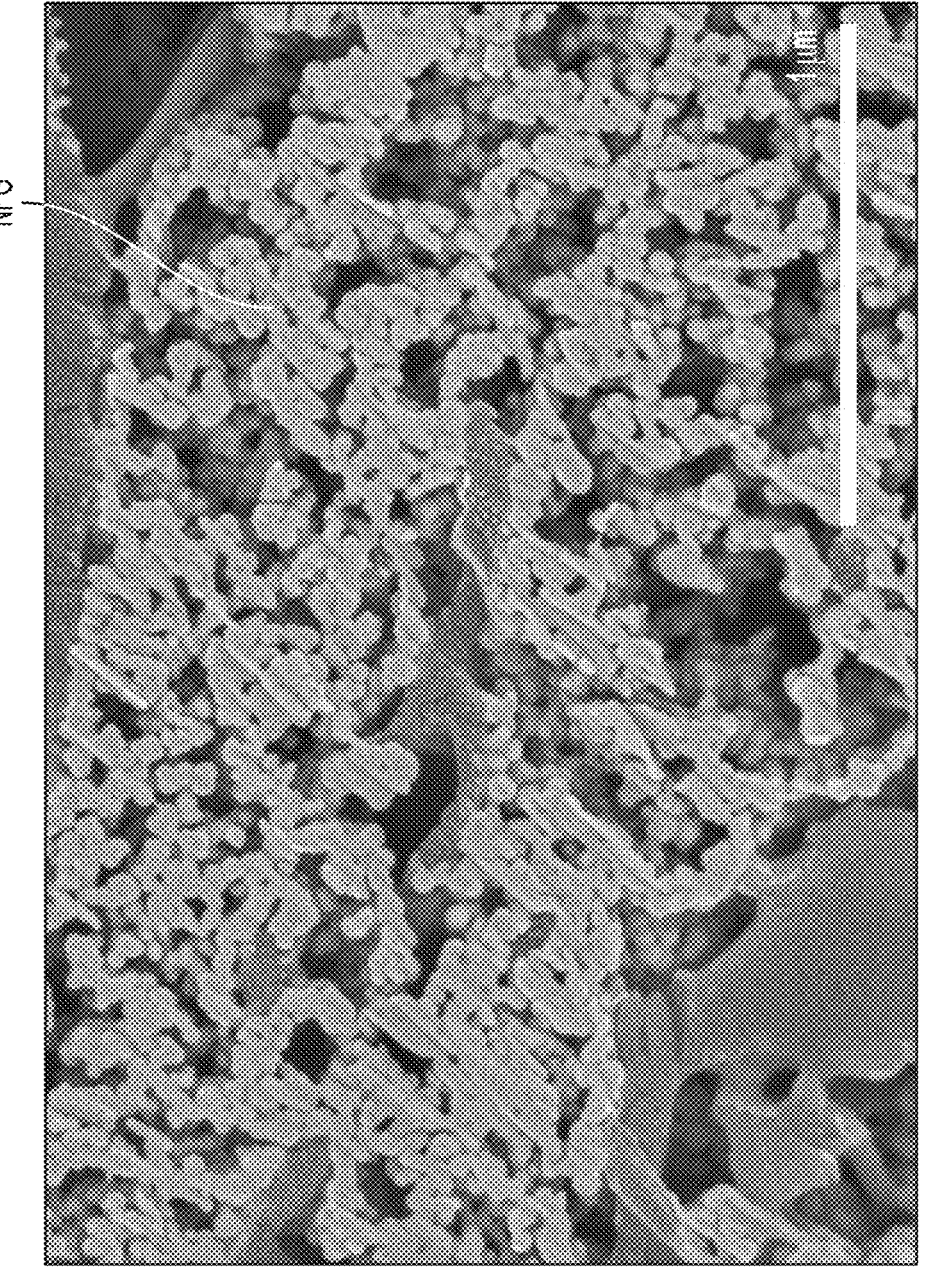

FIGS. 3A-3C show representative SEM images of an example of the NPG/ePTFE composite. FIG. 3A shows a composite cross-section, FIG. 3B shows a surface image, and FIG. 3C shows a close-up of a cross-section of the NPG phase.

The NPG/ePTFE composite comprised a nanoporous, high-surface area gold matrix with a nanopore size distribution of about 10-200 nm within the metal phase. This NPG matrix was imbibed within the interior microstructure of the ePTFE membrane. The NPG is visible as the light-colored material in the pores between the nodes and fibrils of the ePTFE membrane in FIGS. 3A-3C. As shown in FIGS. 3A and 3C, the NPG matrix was shown to be spaced apart from and avoid substantial contact with the ePTFE membrane, especially the nodes of the ePTFE membrane, to form gaps of about 10 μm that are exposed along the surface of the NPG/ePTFE composite, as shown in FIG. 3B. Also, the NPG matrix was absent from the exterior surface layers of the ePTFE membranes (i.e., bare) without the need for laminated interfaces. The NPG/ePTFE composite had a measured sheet resistance of about 0.3-1 ohm/square, according to 4-point probe Sheet Resistance test method described above and shown in FIG. 2.

Figure 4A:
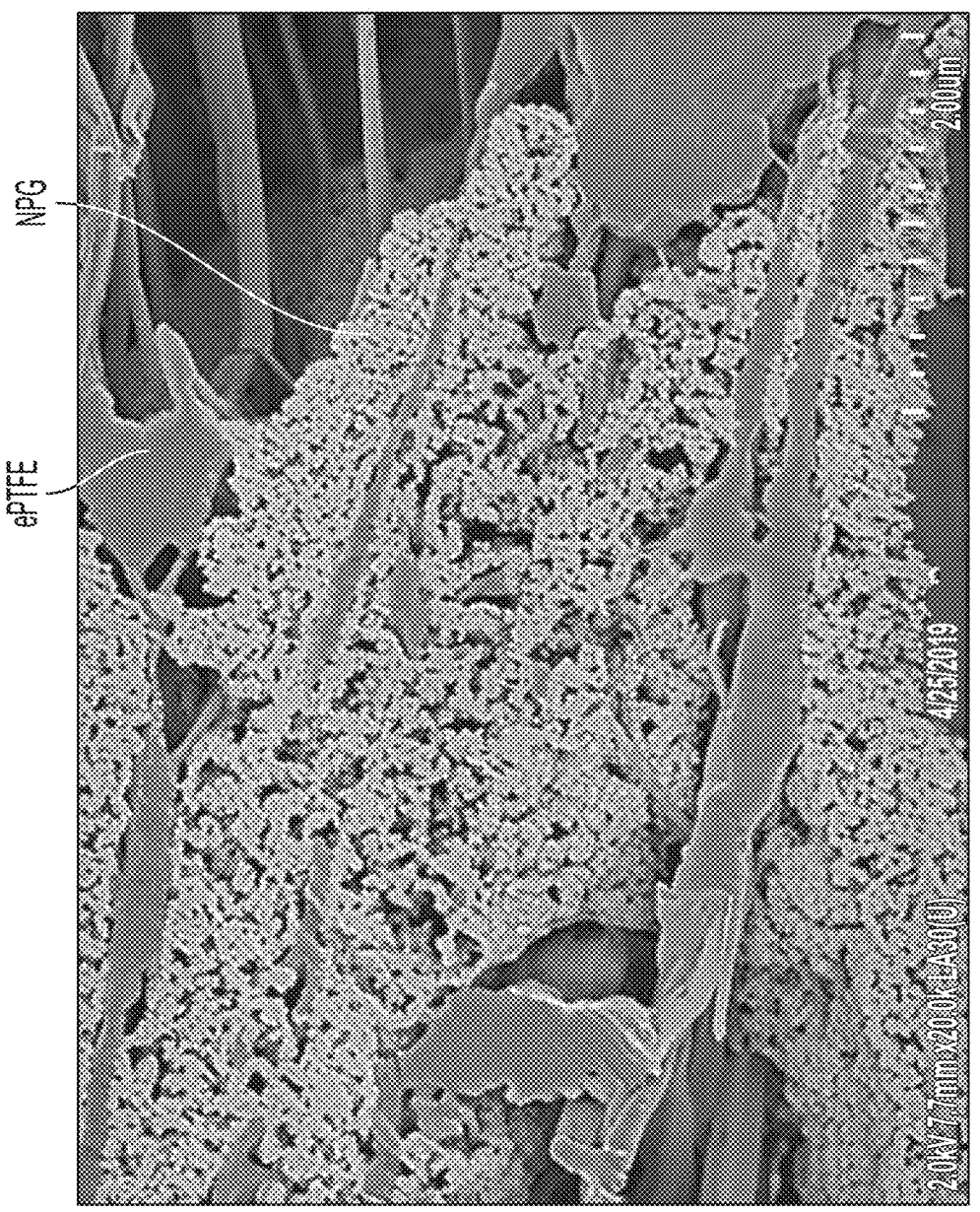
FIG. 4A is another cross-sectional SEM image of the NPG/ePTFE composite of Example 1.
Figure 4B:
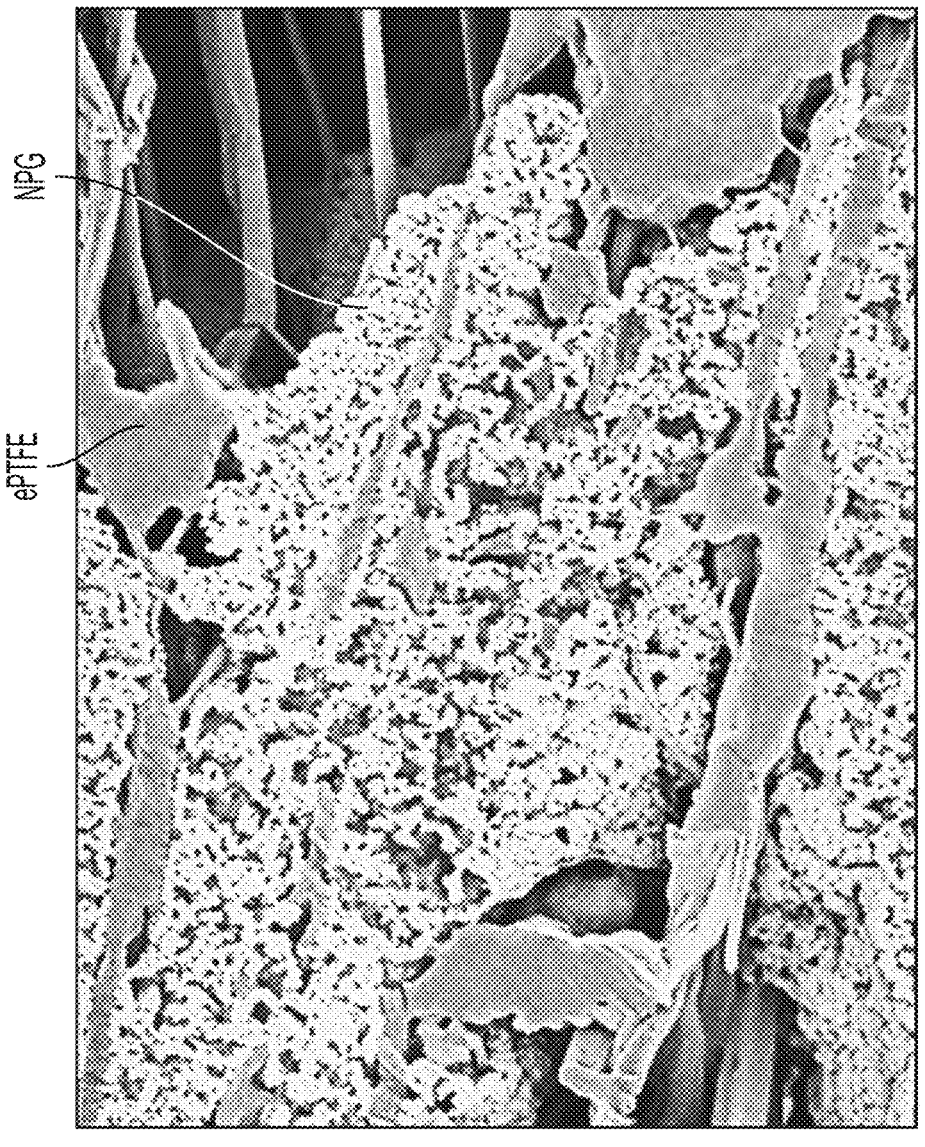
FIG. 4B shows the same image processed for nanopore size analysis.
Figure 4C:
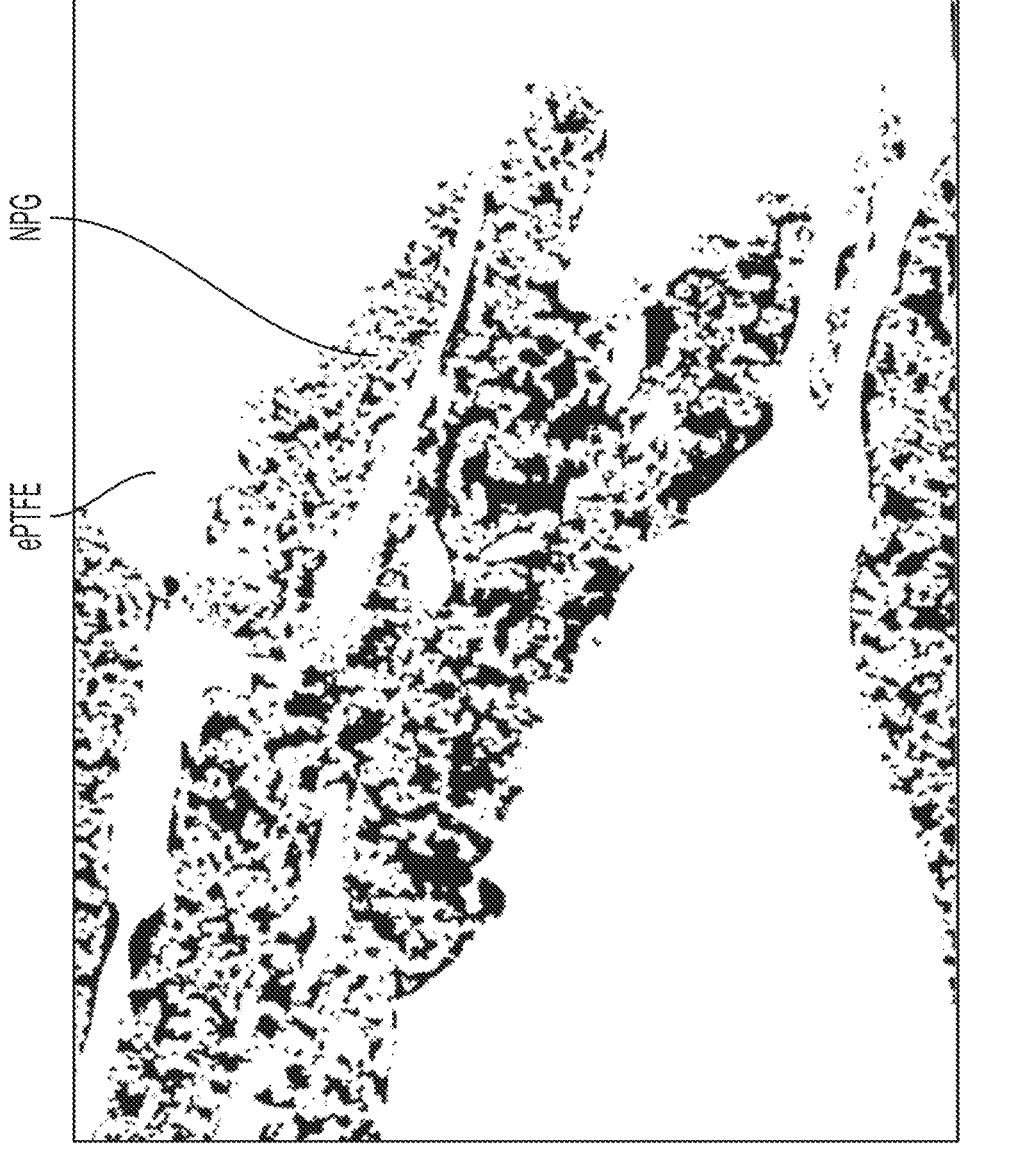
FIG. 4C shows the same image once the nanopores have been isolated.
Figure 5:
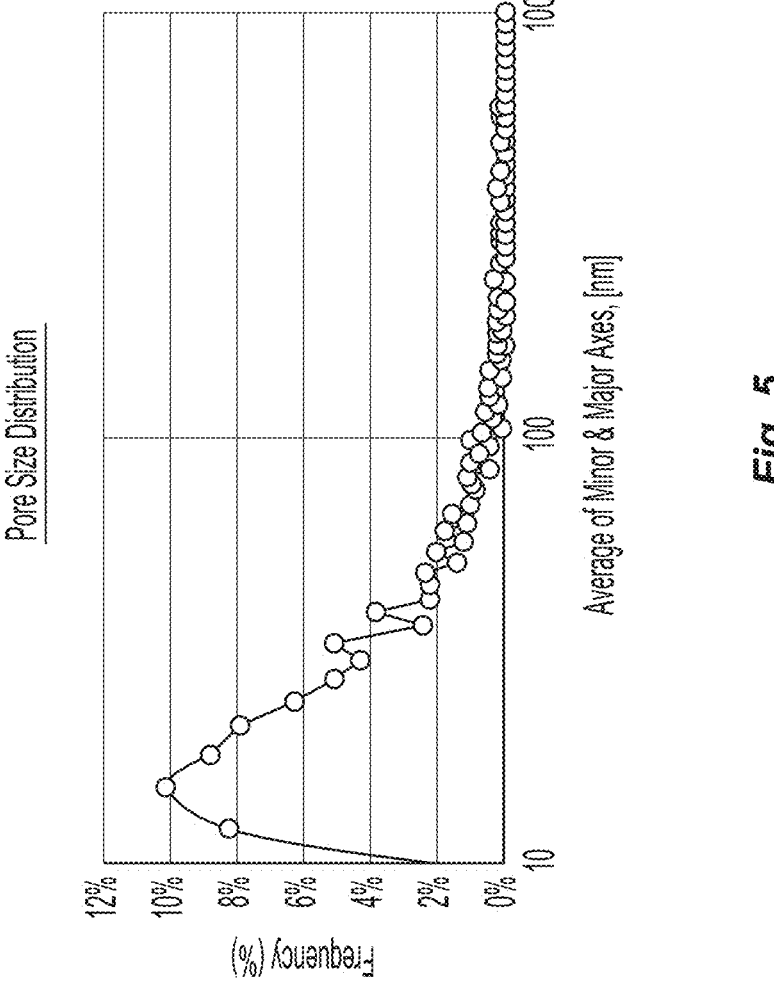
FIG. 5 is a histogram showing the nanopore size distribution within the metal phase of the NPG/ePTFE composite of Example 1.
Figure 6:
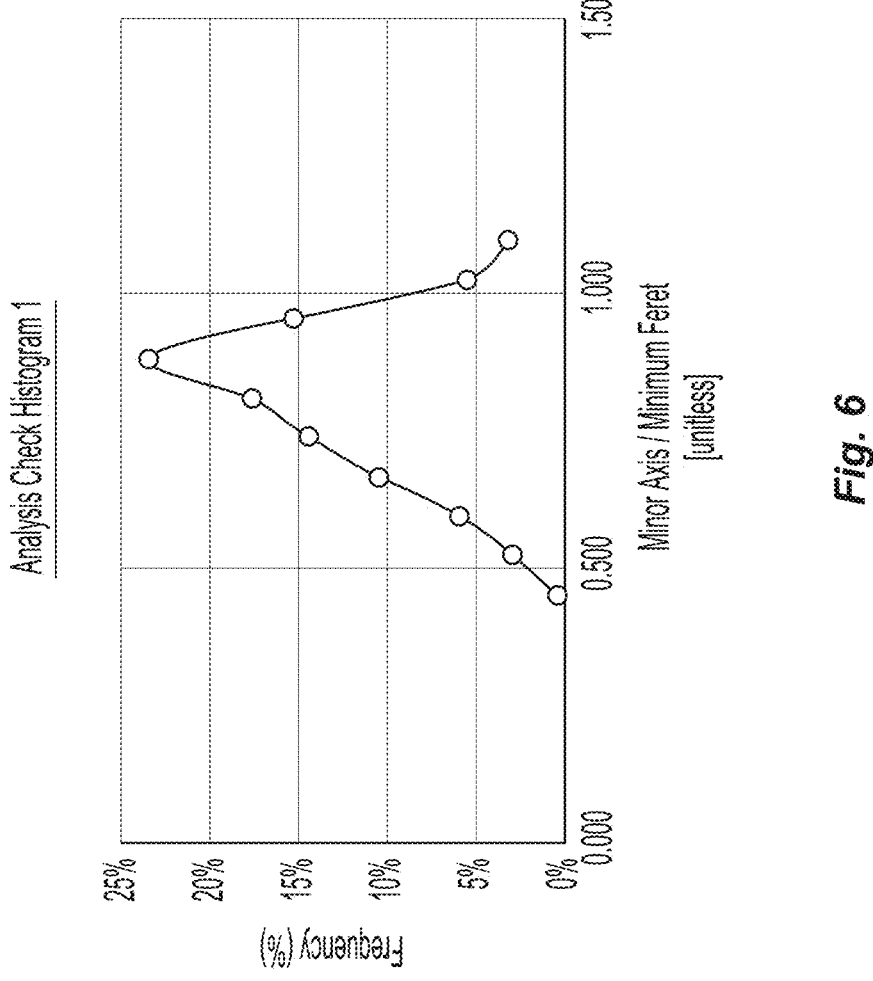
FIG. 6 is a histogram showing the ratio of the minor axis to the minimum feret of the pores within the metal phase of the NPG/ePTFE composite of Example 1.
Figure 7:
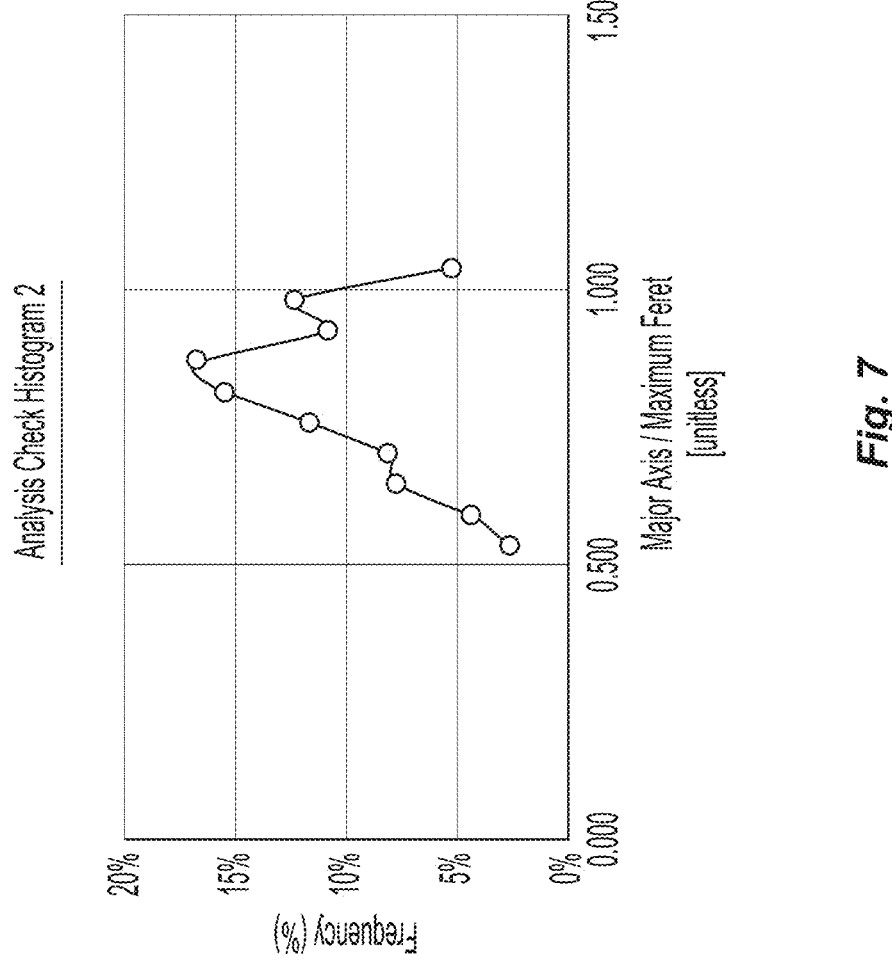
FIG. 7 is a histogram showing the ratio of the major axis to the maximum feret of the pores within the metal phase of the NPG/ePTFE composite of Example 1.

The nanopore size analysis of the NPG metal phase is summarized in FIGS. 4A-7. FIG. 4A shows another representative cross-sectional SEM image of an example of the NPG/ePTFE composite, and FIG. 4B shows the same image processed for nanopore size analysis. FIG. 4C shows the isolated nanopores within the metal phase of the NPG/ePTFE composite. FIG. 5 shows the nanopore size distribution within the metal phase of the NPG/ePTFE composite. FIG. 6 shows the histogram of the ratio of the minor axis of the best-fit ellipse to the minimum feret of the nanopores within the metal phase of the NPG/ePTFE composite. FIG. 7 shows the histogram of the ratio of the major axis of the best-fit ellipse to the maximum feret of the nanopores within the metal phase of the NPG/ePTFE composite.

Example 2: Preparation of NPG/ePTFE Bare Electrode

This example describes the preparation of a NPG/ePTFE planar disc bare electrode ("NPG/ePTFE bare electrode").

A PTFE hollow rod (1.5" length, 0.5" OD, 0.25" ID) was provided with a proximal opening of 0.25" and a distal opening of 3 to 4 mm. The NPG/ePTFE composite of Example 1 was inserted into the hollow rod via the proximal opening, laid flat against the distal opening, and sealed with an ePTFE gasket, to produce the NPG/ePTFE bare electrode.

Example 3: Preparation of CG/ePTFE Composite

This example describes the preparation of an ePTFE membrane composite incorporated with a conformal gold coating ("CG/ePTFE composite").

A first ePTFE membrane (the "target membrane") (3-5 g/m$^2$ mass/area; 1.5 psi bubble point; 92 μm non-contact thickness; W. L. Gore & Associates) was restrained in a 4" diameter metal hoop and tensioned by hand to remove wrinkles. A second ePTFE membrane (the "portal membrane") (3-5 g/m$^2$ mass/area; 40 psi bubble point; 18 μm non-contact thickness; W.L. Gore & Associates) was restrained in a 6" diameter metal hoop and tensioned by hand to remove wrinkles. The portal membrane was placed on top of the target membrane so that the two membranes were in physical contact and approximately concentric. 0.75 mL of a gold nanoparticle ink (#UTDAu60X; UTDots, Inc.) was pipetted onto the surface of the portal membrane and spread evenly using a disposable pipet bulb, until the imbibing solution had fully wetted both the portal membrane and the target membrane (<30 seconds). Excess ink was removed by wiping the upper surface of the portal membrane with a lint-free cloth. The two imbibed membranes were then separated by separating their respective hoops. The portal membrane was discarded. Then, the target membrane was dried using a heat gun set to 200° F., and then heated in a standard convection oven at 300° C. for one hour. The result was a CG/ePTFE composite.

The CG/ePTFE composite had a mass/area of 46 g/m$^2$ and a sheet resistance of about 0.2-0.4 ohms/square, according to 4-point probe Sheet Resistance test method described above and shown in FIG. 2. To demonstrate that the metal was conformally coated throughout the entire thickness of the target membrane, the composite's sheet resistance was approximately the same (specifically, within about 15% of the less resistive surface) whether measured on the top or bottom surface.

Figure 8A:
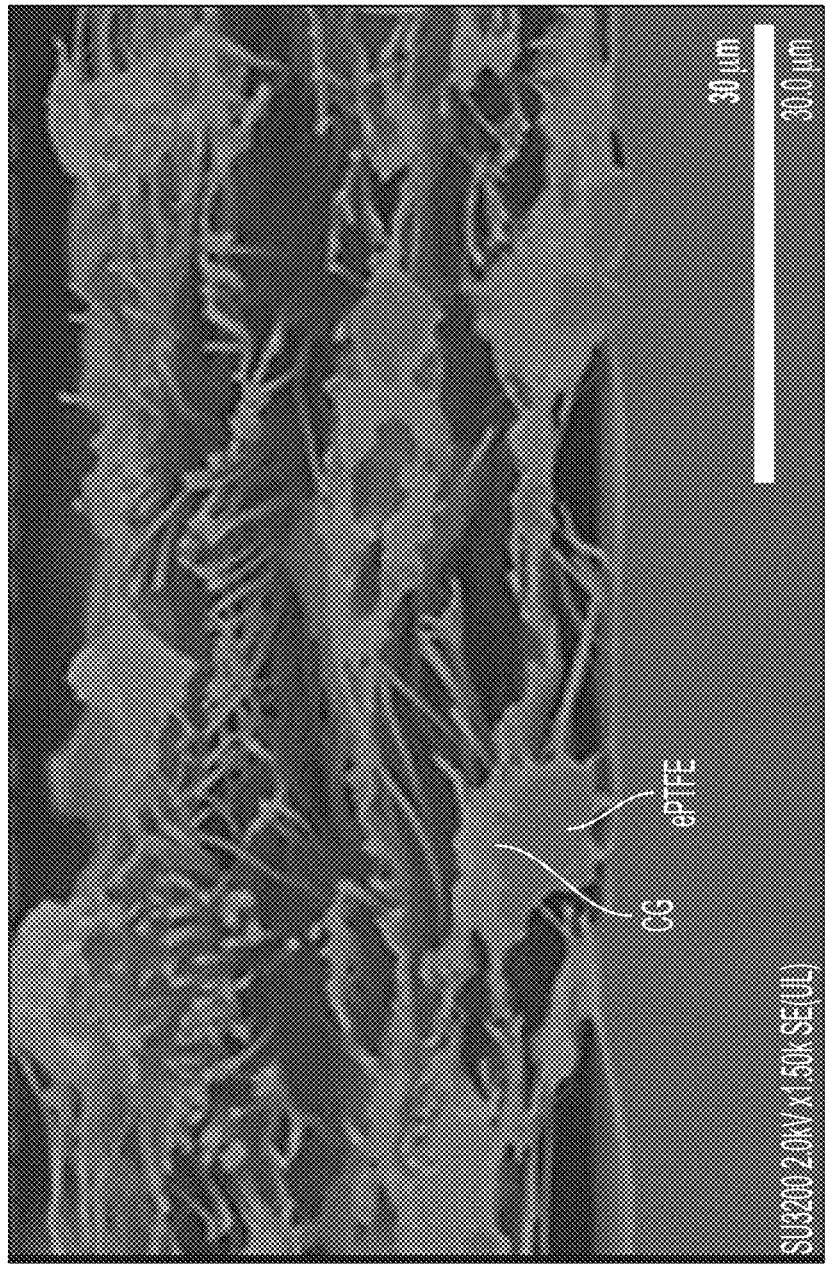
FIGS. 8A-8D are SEM images showing the microarchitecture of conformal gold (CG)/ePTFE composite of Example 3.
Figure 8B:
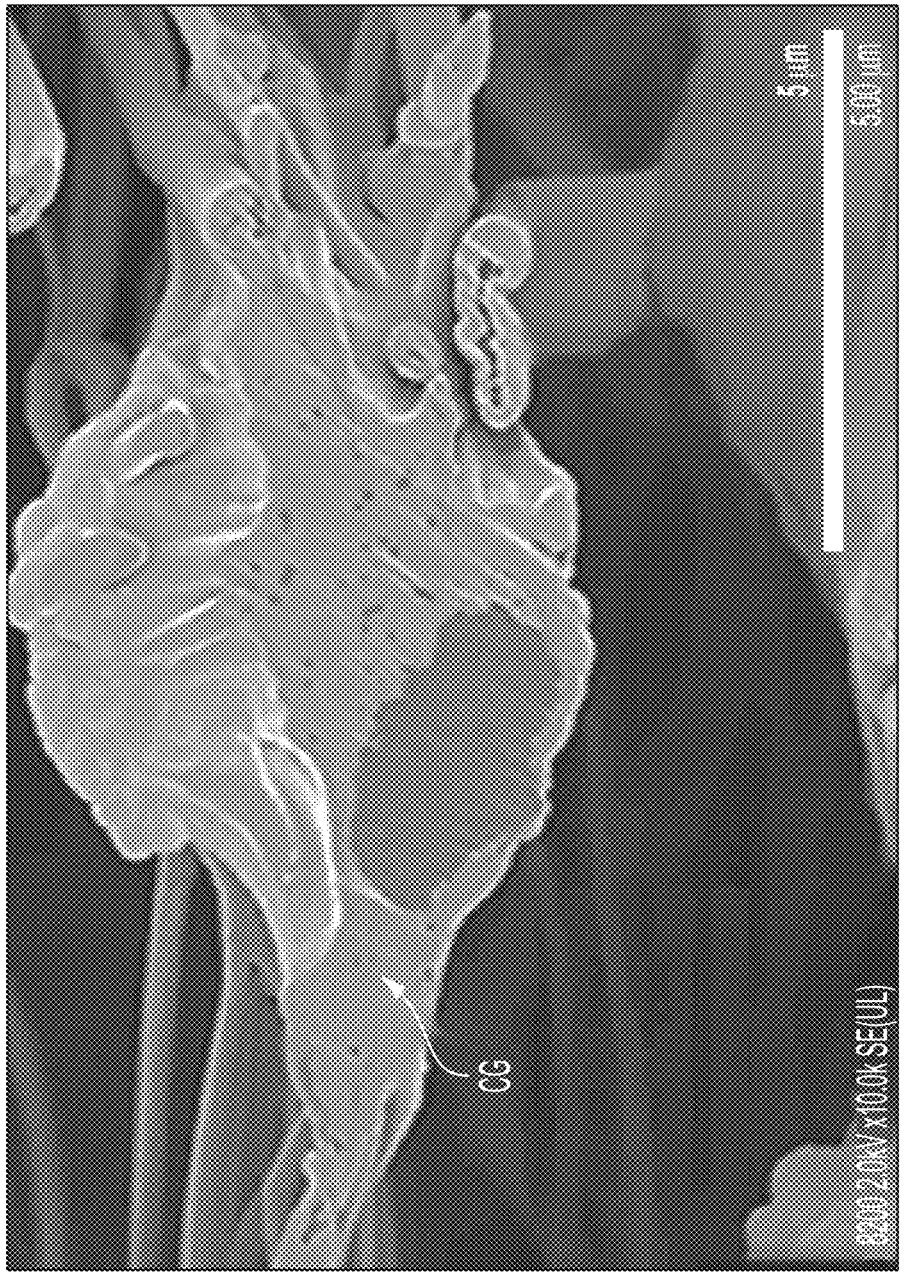
Figure 8C:
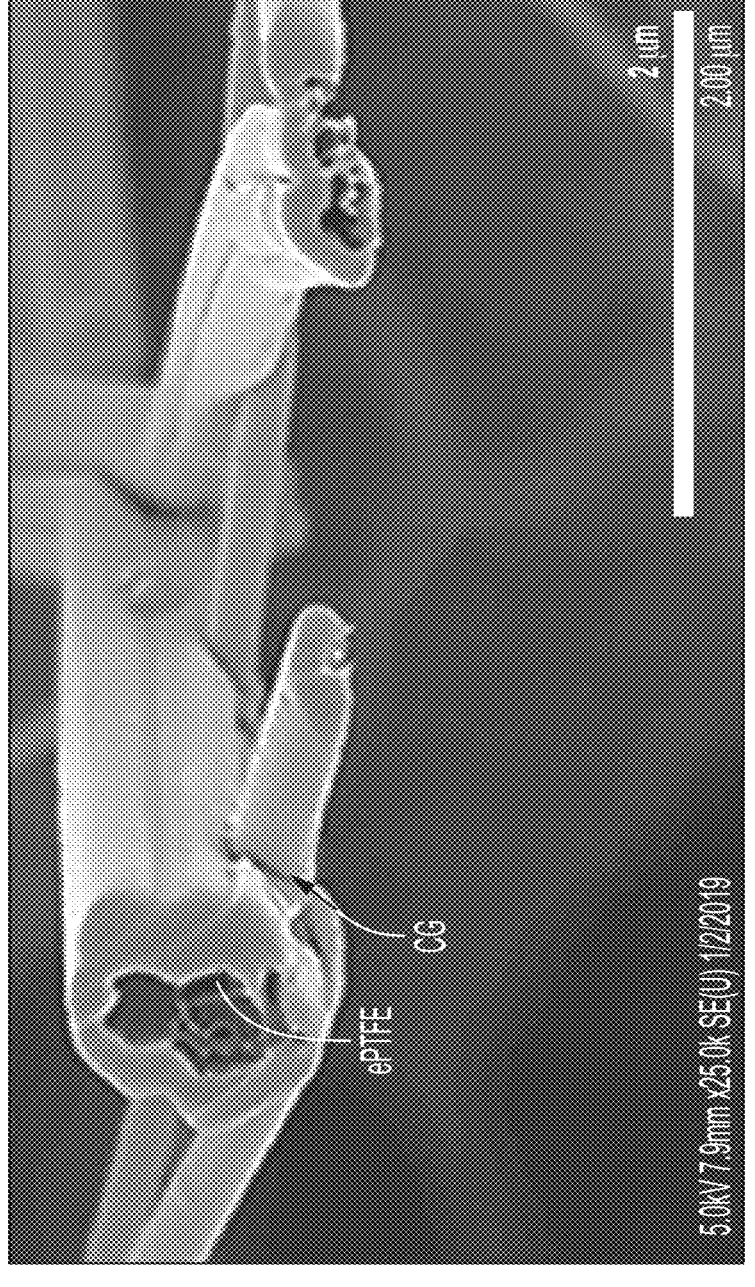
Figure 8D:
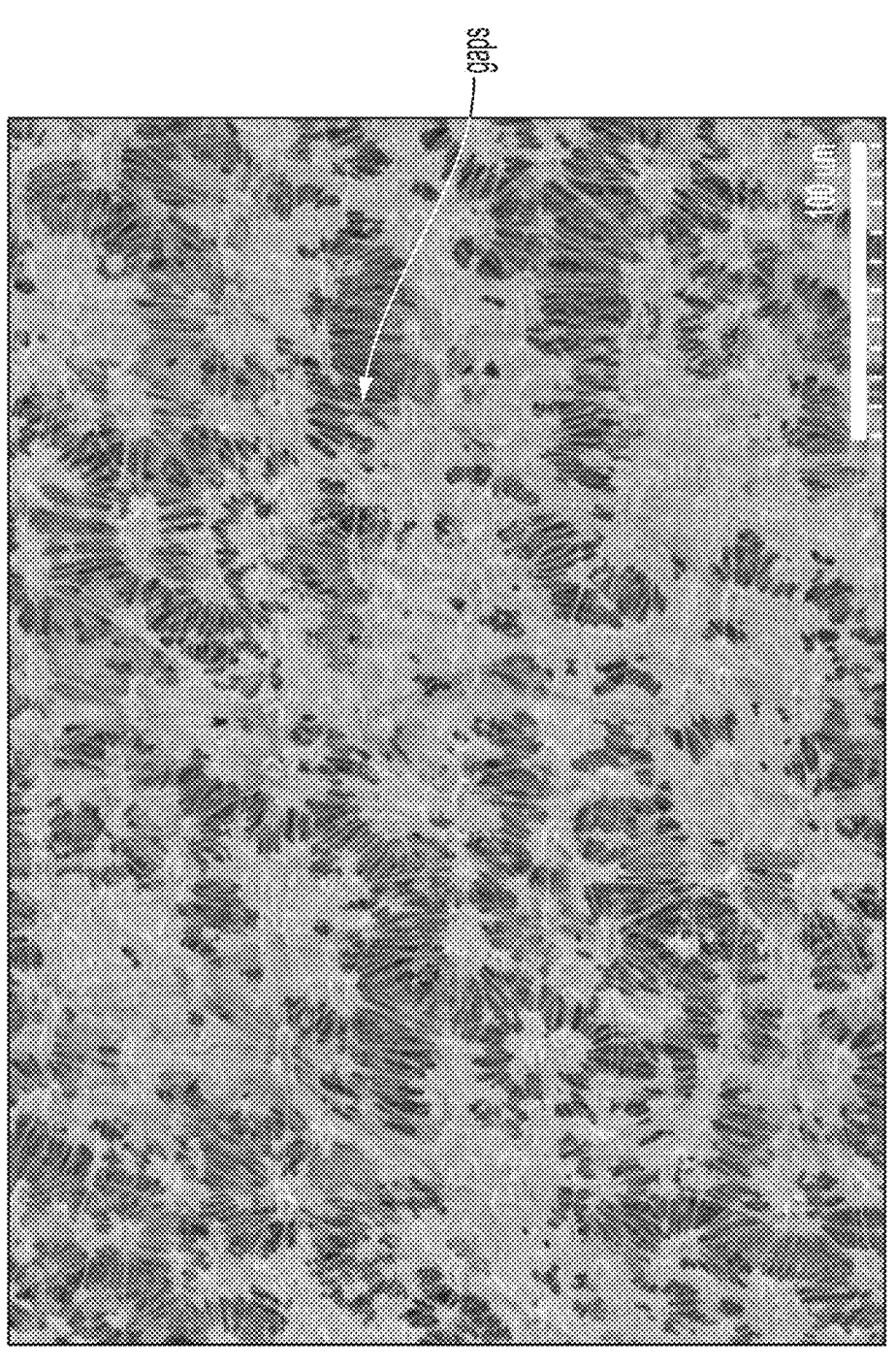

FIGS. 8A-8D show representative SEM images of an example of the CG/ePTFE composite. FIG. 8A shows a composite cross-section, FIG. 8B shows its node cross-section, and FIG. 8C shows its fibril cross-section. The CG is visible around the nodes and fibrils of the ePTFE membrane. FIG. 8D shows a surface image with gaps in the conformal gold coating along the thickness or z-direction that may enable tissue ingrowth while maintaining electrical conductivity in at least the in-plane or x-y direction.

Example 4: Preparation of Silver-Imbibed ePTFE Construct

This example describes the preparation of a silver-imbibed ePTFE construct.

A portal membrane and a target membrane were prepared as in Example 3 above. 5.7 g of a silver nanoparticle ink (#UTDAg60x; UTDots, Inc.) was diluted with 3.3 g of xylene, and was pipetted onto the surface of the portal membrane, spread evenly, and allowed to fully wet the membranes as in Example 3 above. The portal membrane was removed and discarded as in Example 3 above, and the target membrane was heated as in Example 3 above. The result was a silver-imbibed ePTFE construct.

Example 5: Preparation of CG/ePTFE Bare Electrode

This example describes the preparation of a CG/ePTFE planar disc bare electrode ("CG/ePTFE bare electrode").

A PTFE hollow rod (1.5" length, 0.5" OD, 0.25" ID) was provided with a proximal opening of 0.25" and a distal opening of 3 to 4 mm. The CG/ePTFE composite of Example 3 was inserted into the hollow rod via the proximal opening, laid flat against the distal opening, and sealed with an ePTFE gasket, to produce the CG/ePTFE bare electrode.

Example 6: Electrochemical Behavior of Biosensor with NPG/ePTFE Working Electrode and Silver-Imbibed ePTFE Pseudo-Reference Electrode This example describes the electrochemical behavior of a three-electrode electrochemical cell comprising an NPG/ePTFE bare electrode as a working electrode and a silver-imbibed ePTFE construct as a pseudo-reference electrode.

Using the Pseudo-Reference Electrode test method above, a first electrochemical cell was constructed comprising the NPG/ePTFE bare electrode of Example 2 as a working electrode and the silver-imbibed ePTFE construct of Example 4 as a pseudo-reference electrode ("NPG//Ag Imbibed RE"). For comparison, a second electrochemical cell was constructed comprising a planar gold electrode disk working electrode, and a liquid junction Ag/AgCl reference electrode ("Gold Disk-Ag/Ag liquid junction RE")

Figure 9:
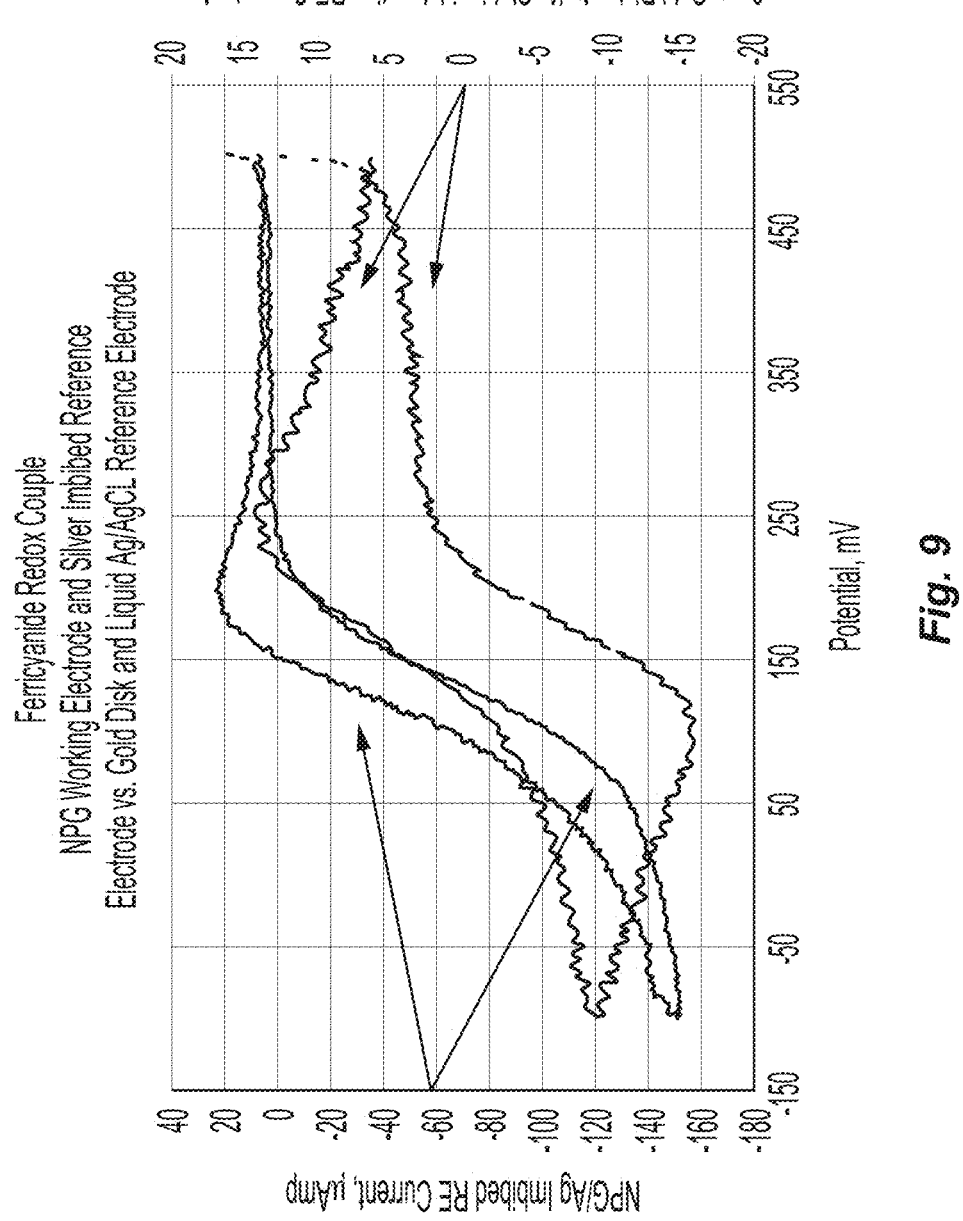
FIG. 9 is a graph showing the cyclic voltammogram of the NPG/ePTFE working electrode/silver-imbibed pseudo-reference electrode of Example 6.

FIG. 9 overlays the cyclic voltammograms of the NPG//Ag Imbibed RE electrochemical cell and the Gold Disk-Ag/Ag liquid junction RE electrochemical cell. As seen from this overlay of data, the cyclic voltammograms are positioned in approximately the same potential region. There is a slight shift in potentials (166 mV vs 124 mV) which is expected as the liquid junction reference electrode is saturated potassium chloride, whereas the pseudo-reference electrode is in direct contact with the electrolyte. Also as seen, the hysteresis in the voltammogram for the NPG//Ag Imbibed RE cell is narrower and has higher gain, compared to that for the Gold Disk-Ag//AgCl liquid junction RE cell, demonstrating the NPG//Ag Imbibed RE cell that employs a pseudo-reference electrode acts predictably within these defined conditions. In other words, an electrode design using ePTFE as a working electrode substrate with nanoporous gold, ePTFE as a pseudo-reference electrode substrate with imbibed silver, and a physical separation between them, can function as an electrochemical analyte biosensor.

Example 7: Biofouling Resistance of NPG/ePTFE Bare Electrode

This example describes the resistance against biofouling of a NPG/ePTFE bare electrode.

The NPG/ePTFE bare electrode of Example 2 was examined for biofouling resistance, according the Biofouling Resistance test method above. In addition, an unpolished gold foil sample was subjected to the same testing conditions Table 3 shows the peak currents of the NPG/ePTFE bare electrode compared to the gold foil sample, normalized to the baselines for each sample. The NPG/ePTFE samples showed only a slight reduction of peak current in the BSA biofouling test solutions, even at the highest BSA concentrations. In comparison, the gold foil samples had a significant reduction of peak currents even at low BSA concentrations. In summary, the NPG/ePTFE samples exhibited high electrochemical performance in the presence of common biofouling media.

TABLE 3

| | Control | BSA (2 g/mL) | BSA (6 g/mL) | BSA (10 g/mL) | BSA (15 g/mL) | BSA (25 g/mL) |
|---|---|---|---|---|---|---|
| NPG/ePTFE | 1 | 0.999 | 0.978 | 0.962 | 0.929 | 0.882 |
| Gold Foil | 1 | 0.381 | 0.320 | 0.283 | 0.243 | 0.212 |

Example 8: Preparation of NPG/ePTFE GOx and CG/ePTFE GOx Finished Electrodes

This example describes the preparation of enzyme-immobilized finished electrodes comprising glucose oxidase (GOx). All solutions are aqueous unless otherwise specified.

The distal end of each of the NPG/ePTFE bare electrode of Example 2 and the CG/ePTFE bare electrode of Example 5 was immersed in isopropanol, rinsed in deionized water, immersed in a polyethyleneimine (PEI) solution (10 mg/mL water; 10 min; Sigma), and rinsed with deionized water. GOx (50 kU/g activity; Sigma) was dissolved in phosphate buffer at 500 U/mL, and 10 μL was pipetted via each electrode's distal opening onto its ePTFE membrane surface and air dried. The distal end of each electrode was immersed a second time in the PEI solution, pipetted a second time with the GOx solution, and air dried a second time. A 4 μL volume of Nafion solution (2% w/v in 92 wt % ethanol:8 wt % water; Sigma) was pipetted onto each electrode's distal opening, air dried, and stored at 4° C., to produce a NPG/ePTFE GOx finished electrode or a CG/ePTFE GOx finished electrode, respectively.

Example 9: Electrochemical Responses of NPG/ePTFE GOx and CG/ePTFE GOx Finished Electrodes to Glucose This example describes the electrochemical responses of the NPG/ePTFE GOx and CG/ePTFE GOx finished electrodes of Example 8 to glucose.

Figure 10B:
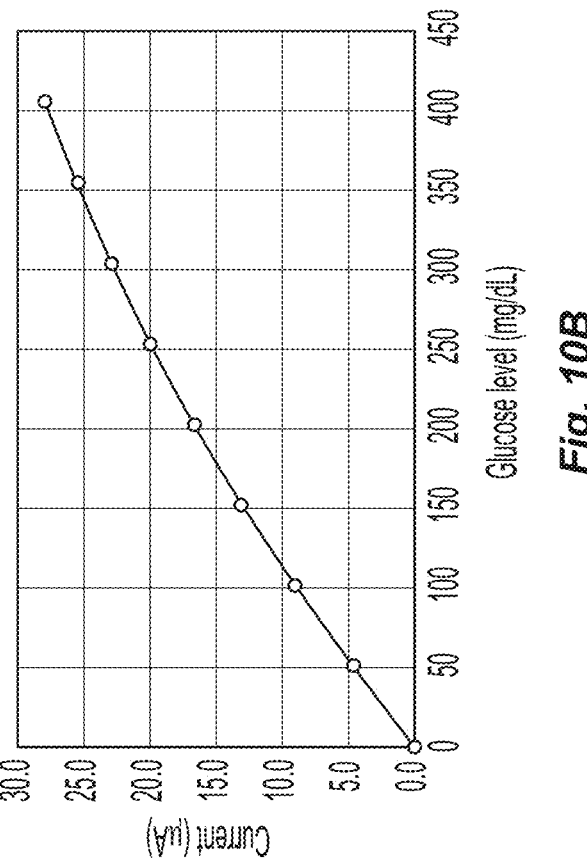
FIGS. 10A and 10B are graphs showing glucose response of the GOx-based glucose sensor comprising the NPG/ePTFE material of Example 9.
Figure 10A:
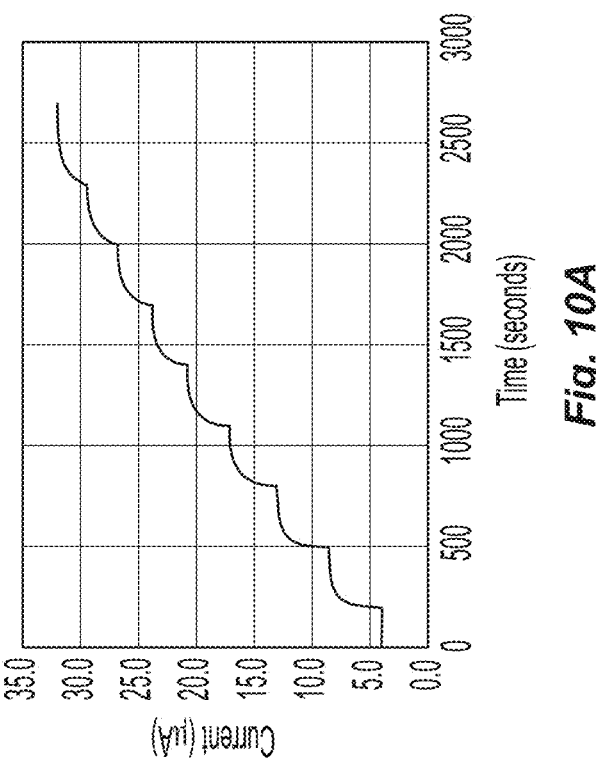

As shown in FIG. 10A, immediately upon the serial addition of glucose, the measured current of the NPG/ePTFE GOx finished electrode rose rapidly and quickly stabilized. As shown in FIG. 10B, the NPG/ePTFE GOx finished electrode responded to a wide range of glucose concentrations from 0 to 400 mg/dL. In comparison, a gold foil immobilized with glucose oxidase prepared according to the procedure of Example 8 showed a greatly reduced signal as a function of glucose concentration (not shown).

Figure 11B:
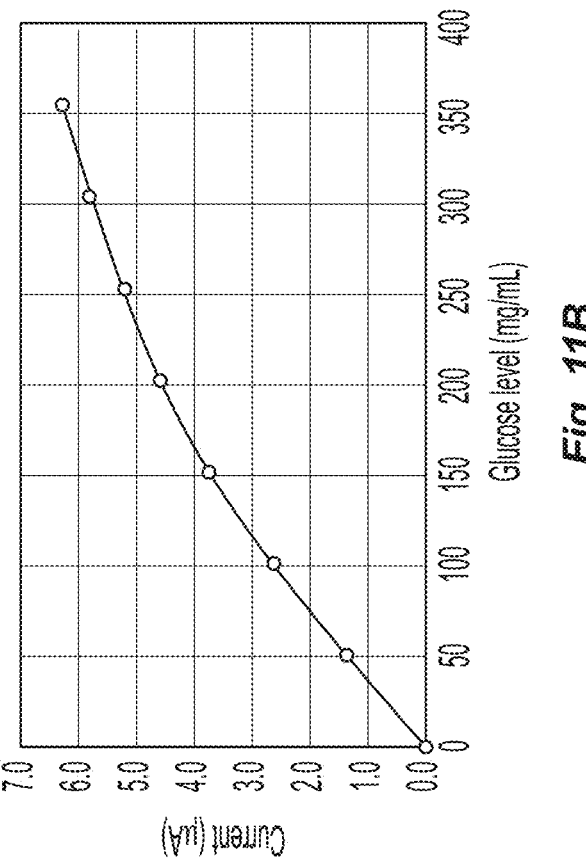
FIGS. 11A and 11B are graphs showing glucose response of the GOx-based glucose sensor comprising the CG/ePTFE material of Example 9.
Figure 11A:
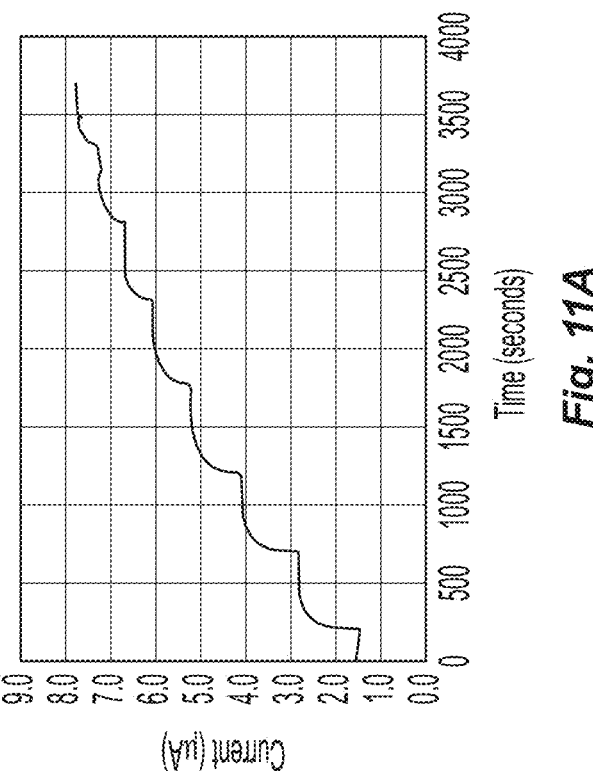

As shown in FIG. 11A, immediately upon the serial addition of glucose, the measured current of the CG/ePTFE GOx finished electrode rose rapidly and quickly stabilized. As shown in FIG. 11B, the CG/ePTFE GOx finished electrode responded to a wide range of glucose concentrations from 0 to 400 mg/dl. In comparison, a gold foil immobilized with glucose oxidase prepared according to the procedure of Example 8 showed a greatly reduced signal as a function of glucose concentration (not shown).

Example 10: Electrochemical Surface Area Dependency on Electrolyte Solvent Surface Tension This example describes the electrochemical surface area dependency on electrolyte solvent surface tension.

Each of the NPG/ePTFE composite of Example 1, the CG/ePTFE composite of Example 3, and a gold foil was immersed in a series of solutions comprising varying ratios of saline to isopropanol. Saline has a high surface tension of about 72 mN/m, isopropanol has a lower surface tension of about 21 mN/m, and mixtures of saline:isopropanol have surface tensions as a function of the ratios of the solvents, such that a 50:50 saline:isopropanol mixture has a low surface tension of about 25 mN/m, and a 90:10 saline: isopropanol mixture has a high surface tension of about 50 mN/m, or about the same as blood).

The electrolytes were prepared as follows. All dilutions used DI water (>18 megaohm). 0.05 M Sulfuric Acid ($H_2SO_4$) in DI water: 2.5 mL of 1 M $H_2SO_4$ diluted to 50 mL. 0.05 M Sulfuric Acid in 1% Isopropanol: 2.5 mL of 1 M $H_2SO_4$ and 0.5 mL isopropanol diluted to 50 mL. 0.05 M Sulfuric Acid in 5% Isopropanol: 2.5 mL of 1 M $H_2SO_4$ and 2.5 mL isopropanol diluted to 50 mL. 0.05 M Sulfuric Acid in 10% Isopropanol: 2.5 mL of 1 M $H_2SO_4$ and 5 mL isopropanol diluted to 50 mL. 0.05 M Sulfuric Acid in 20% Isopropanol: 2.5 mL of 1 M $H_2SO_4$ and 10 mL isopropanol diluted to 50 mL. 0.05 M Sulfuric Acid in 30% Isopropanol: 2.5 mL of 1 M $H_2SO_4$ and 15 mL isopropanol diluted to 50 mL. 0.05 M Sulfuric Acid in 50% Isopropanol: 2.5 mL of 1 M $H_2SO_4$ and 25 mL isopropanol diluted to 50 mL.

The electrochemical surface area of each immersed sample was measured, and the absolute change in the measured electrochemical surface area was calculated according to the following equation:

$$\text{absolute change} = \text{abs}\big((H - L)/H\big) * 100\%$$

where:
 abs(n) is the absolute value function;
 L is the measured electrochemical surface area in a low surface tension solvent comprising 50:50 saline: isopropanol of about 25 mN/m; and
 H is the measured electrochemical surface area in a high surface tension solvent comprising saline of about 72 mN/m.

Figure 12:
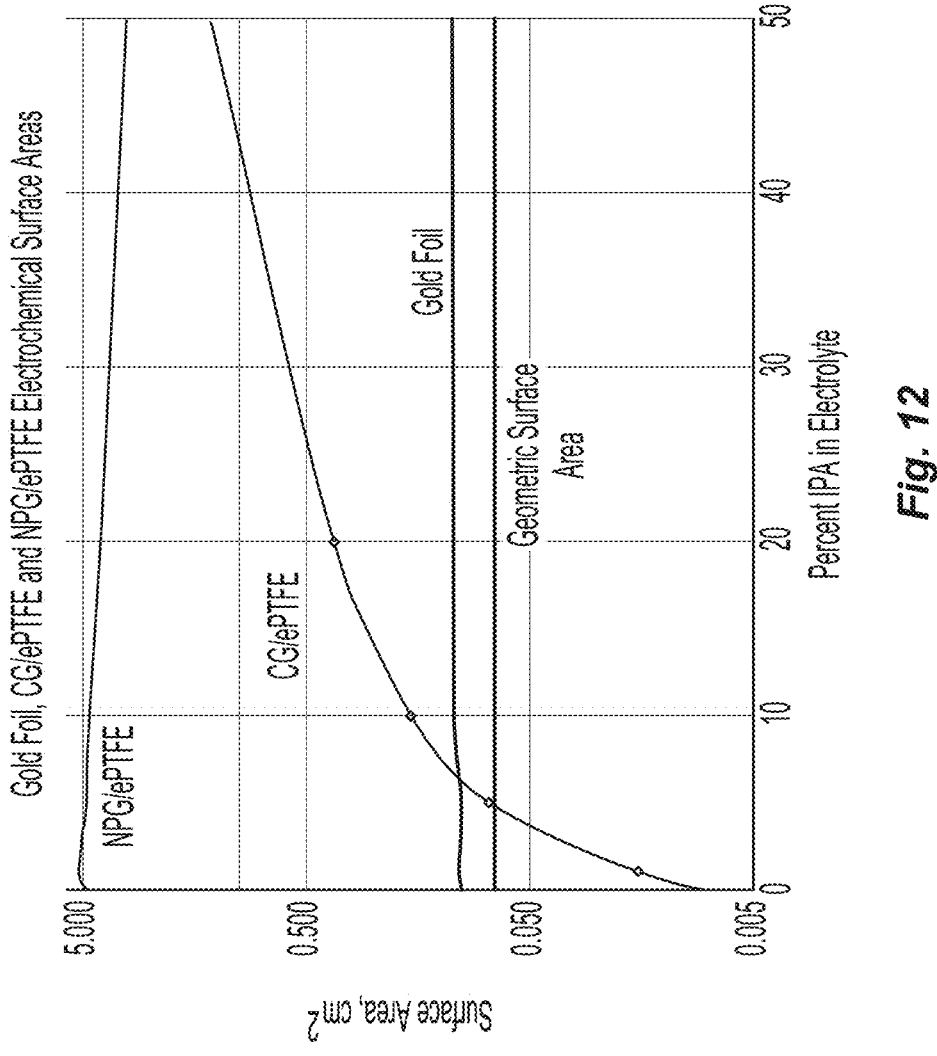
FIG. 12 is a graph showing the electrochemical surface area dependency on electrolyte solvent surface tension of Example 10.

As shown in FIG. 12, the composites showed significant differences depending on the electrolyte composition. The CG/ePTFE composite exhibited increasing surface area results with decreasing electrolyte surface tension across the range of pure saline to 50:50 saline:isopropanol, wherein the electrochemical surface area increased from about 0.005 $cm^2$ to about 1.000 $cm^2$ (or an absolute change of about 19,900%) over this range. In comparison, the NPG/ePTFE composite demonstrated its electrochemical surface area to have little dependence on electrolyte surface tension, and produced a relatively flat response across the range of pure saline to 50:50 saline:isopropanol, wherein the electrochemical surface area varied from about 5 $cm^2$ to about 2.5 $cm^2$ (or an absolute change of about 50%) over this range. As discussed above, this flat response for NPG/ePTFE was not expected to be relatively constant (i.e. less than about 50%) over the broad electrolyte surface tension range, as the base ePTFE film was hydrophobic and thus expected to limit wetting and result in lower observable electrochemical surface areas. In contrast, the gold foil, being non-hydrophobic, showed an expected relatively flat response across the range of pure saline to 50:50 saline:isopropanol.

Example 11: Capillary Flow Porometry of NPG/ePTFE Composite

Figure 16:
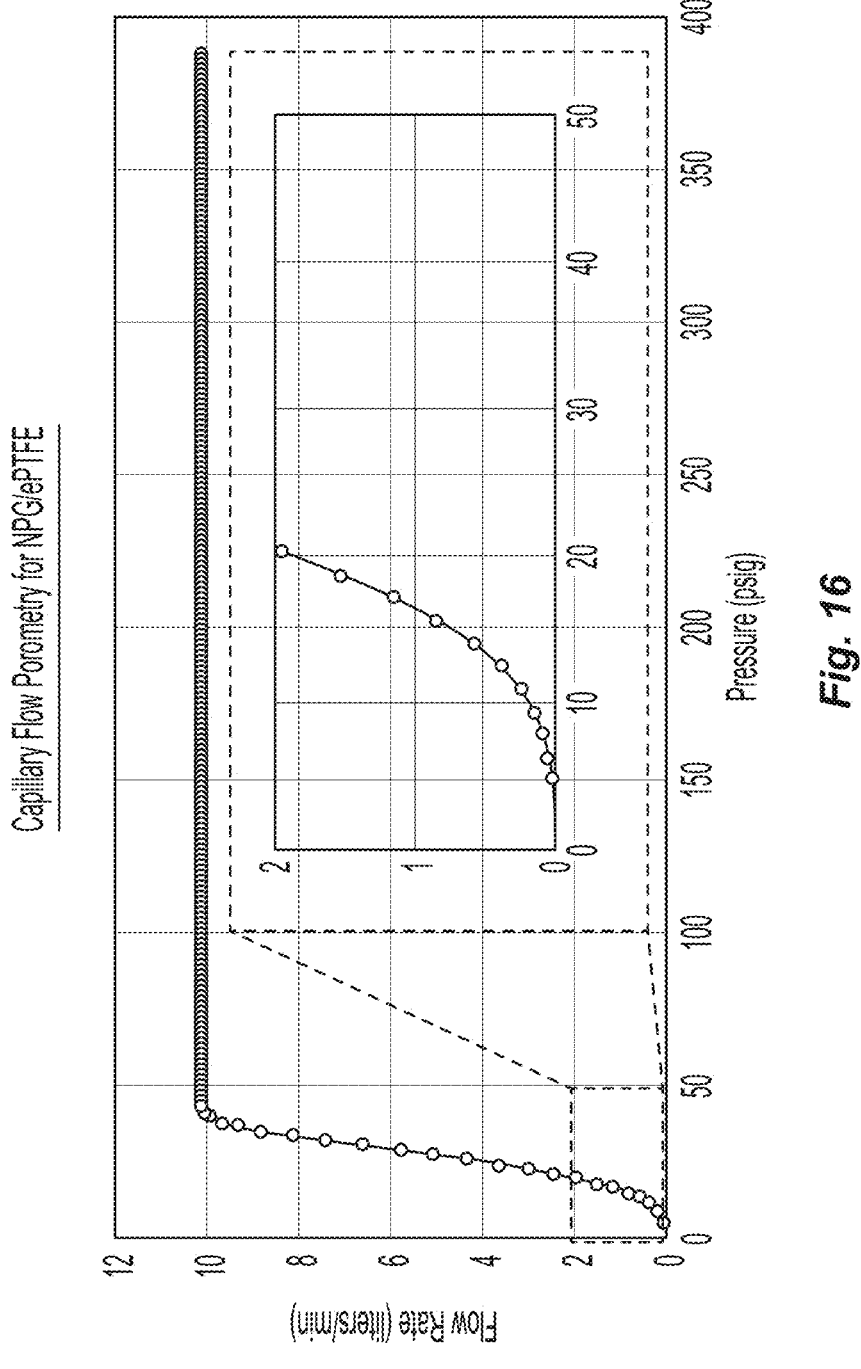
FIG. 16 is a graph showing capillary flow porometry data of Example 11.

This example describes capillary flow porometry (CFP) data of the NPG/ePTFE composite of Example 1 according to the CFP test method above. As explained in Example 1 and shown in FIGS. 3A and 3C, gaps were visible between the NPG matrix and the ePTFE membrane, especially the nodes of the ePTFE membrane. The CFP data is presented in FIG. 16. The very low bubble point (i.e., the onset of flow) is approximately 5 psig, which is consistent with the presence of these gaps between the NPG matrix and the ePTFE membrane extending through the thickness of the composite.

Example 12: Durability of NPG/ePTFE Composite

This example describes durability data of an NPG/ePTFE composite made according to the teachings of Example 1 measured according to the Wet Flex Particulation test method above. Upon completion of the 24-hour Wet Flex Particulation test, the amount of gold present in the test fluid was below the ICP detection limit. This result was consistent with no loss of gold from the NPG/ePTFE composite and indicated that at least 99.97 wt. % of the gold was retained in the composite.

Example 13: Fragility of Thin NPG Without Reinforcement

This example illustrates the difficulty of handling thin NPG that is not reinforced with a polymer substrate. A piece of 12K White Gold Genuine Gold Leaf (L.A. Gold Leaf, 0.12 μm thick, 51% gold/48% Ag/1% Pd), approximately 1 cm×1 cm in size, was placed in a petri dish using tweezers. 70% $HNO_3$ (aq) was added to the petri dish in a quantity sufficient to completely cover the NPG. The gold leaf remained in the $HNO_3$ (aq) for 15 minutes at room temperature to allow time for the silver to be etched away to produce NPG. After etching, the sample readily broke even when lightly touched with the tweezers.

Example 14: Preparation CPS/ePTFE Composite

A close-packed silver/ePTFE composite (CPS/ePTFE) was made according to the teachings of Example 1 of International Publication No. WO 2019/216885 to W.L. Gore & Associates, Inc. titled "Flexible and Durable Printed Circuits on Stretchable and Non-Stretchable Substrates". The properties of this material and of an NPG/ePTFE composite prepared according to the procedure described in Example 1 were measured and compared.

Figure 18:
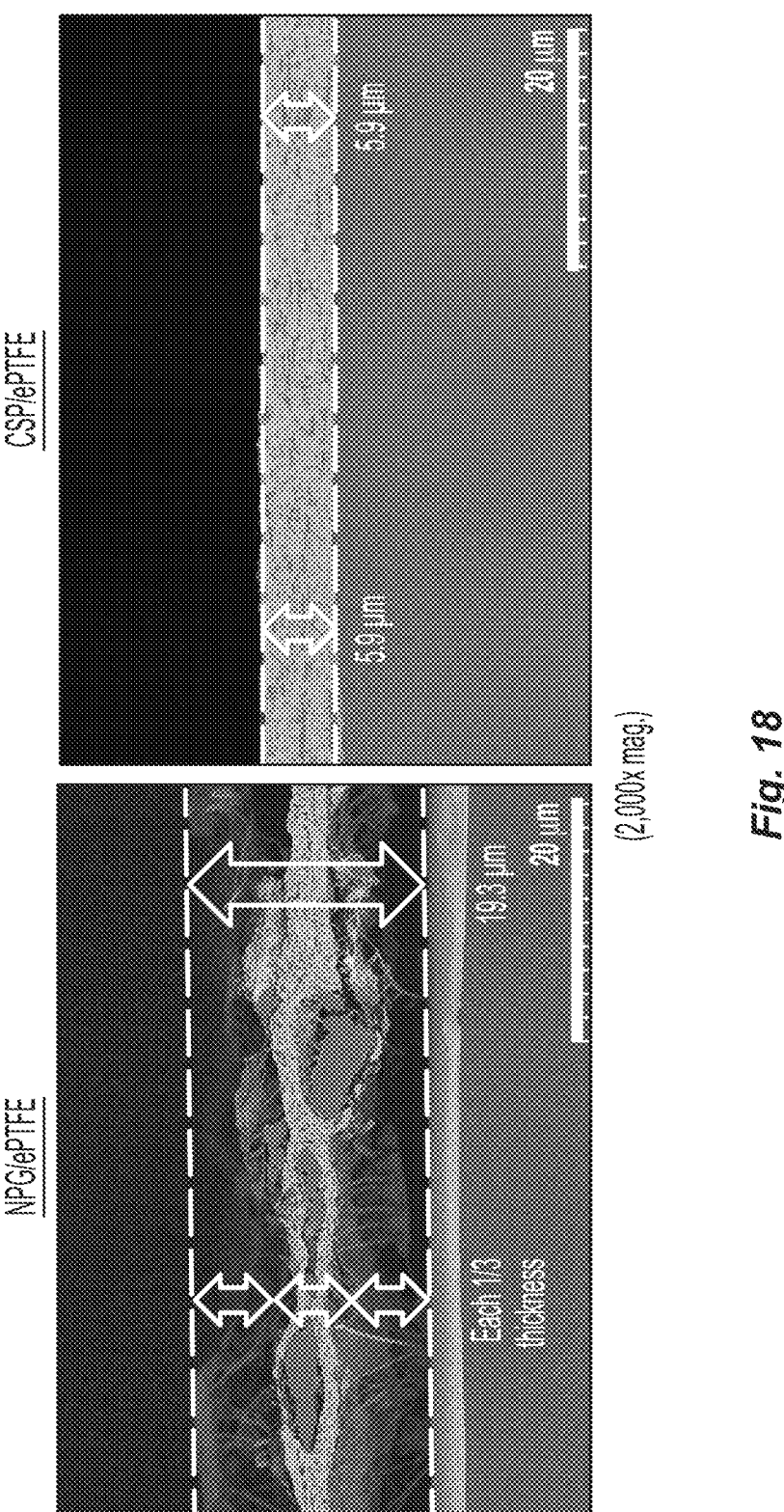
FIG. 18 includes cross-sectional SEM images at 2,000× magnification comparing the NPG/ePTFE composite of Example 1 to a close-packed silver/ePTFE (CPS/ePTFE) composite of Example 14.
Figure 19:
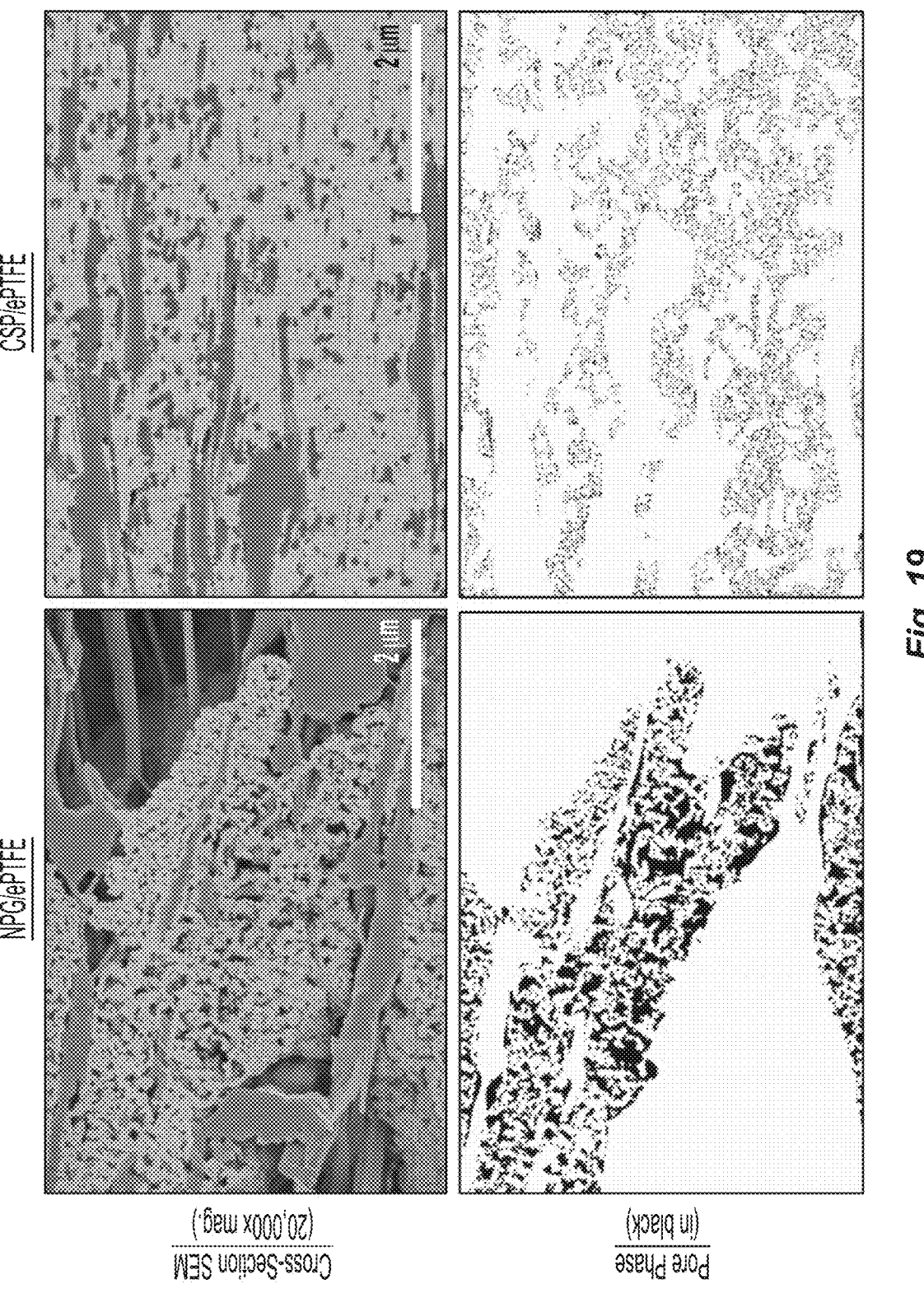
FIG. 19 includes cross-sectional SEM images at 20,000× magnification comparing the NPG/ePTFE composite of Example 1 to the CPS/ePTFE composite of Example 14, and also shows the nanopore phase isolated from the corresponding images for nanopore size analysis.
Figure 20:
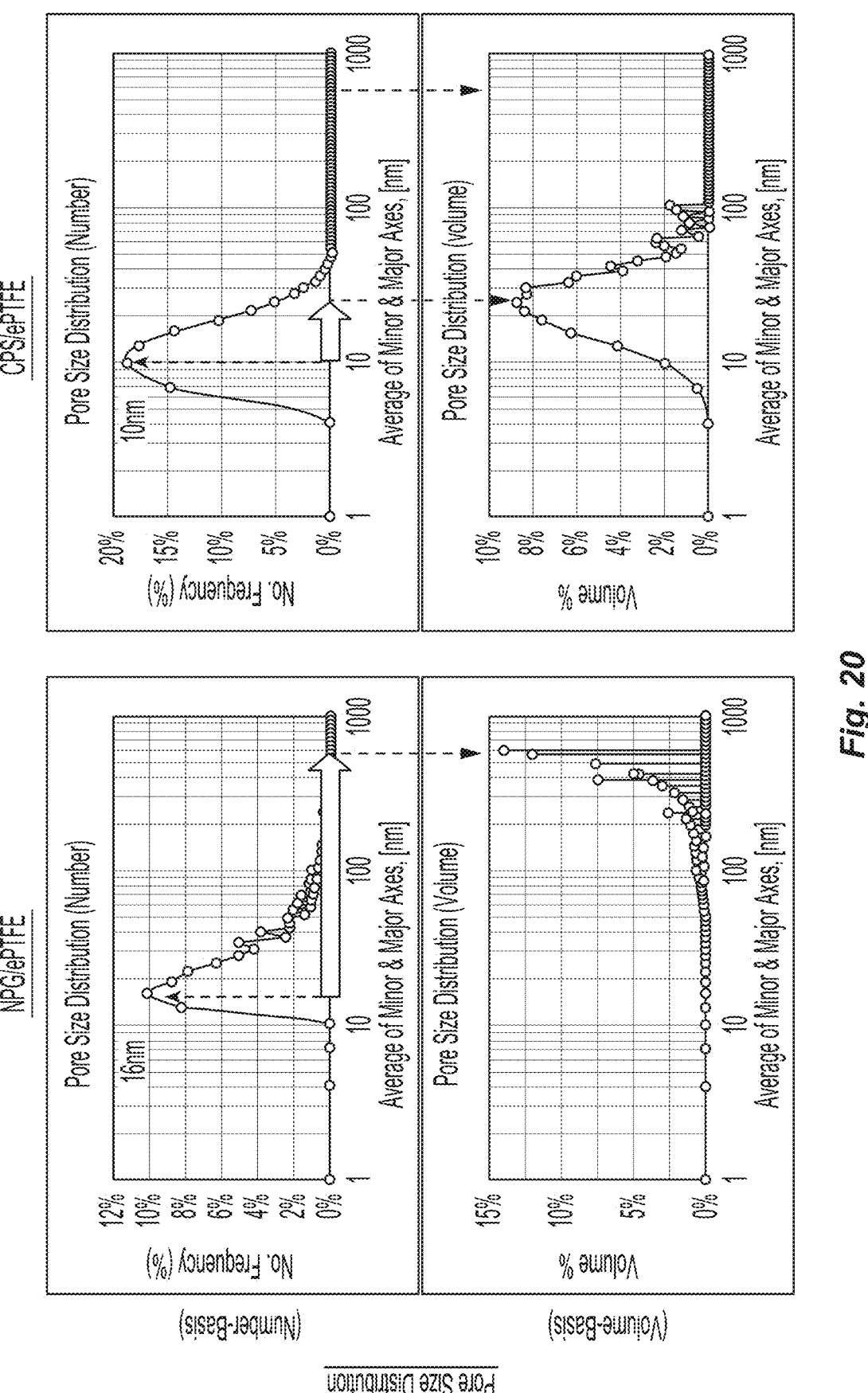
FIG. 20 includes histograms comparing the number-based and volume-based nanopore size distribution within the metal phase of the NPG/ePTFE composite of Example 1 and the CPS/ePTFE composite of Example 14.

FIG. 18 compares the cross-sectional SEM images for NPG/ePTFE and CPS/ePTFE at a low magnification (2,000×) to enable determination of the total thickness of each sample, including the bare ePTFE surface layers of the NPG/ePTFE. FIG. 19 compares a close-up of the metal phases of the NPG/ePTFE and CPS/ePTFE, and their pores phases as determined by quantitative image analysis. FIG. 20 compares the pore size distributions of the NPG/ePTFE and CPS/ePTFE on a number basis and on a volume basis. The mode pore size is indicated on each graph, and the shift in mode from the number-based graph to the volume-based graph is indicated with a block arrow.

Numerical data comparing the NPG/ePTFE and CPS/ePTFE are shown in Tables 4-6. To determine the volume-per-area and volume % values, the following densities were assumed: 19.3 g/cc for gold, 10.5 g/cc for silver, 2.2 g/cc for PTFE. Some key shifts in the pore size distribution are tabulated in Table 7.

TABLE 4

Mass- and Volume-Based Composition

| Property | NPG/ePTFE | CPS/ePTFE |
|---|---|---|
| *Mass Basis* | | |
| Total Mass-per-Area (g/m$^2$) | 31.5 | 32.3 |
| Substrate (ePTFE) Mass-per-Area (g/m$^2$) | 3.7 | 4.6 |
| Metal Mass-per-Area (g/m$^2$) | 27.8 | 27.7 |
| Metal wt % of Total Mass | 88 w % | 86 w % |
| Substrate wt % of Total Mass | 12 w % | 14 w % |
| *Volume Basis* | | |
| Thickness (μm) or Volume-per-Area (cc/m$^2$) | 19.3 | 5.9 |
| Substrate Volume-per-Area (cc/m$^2$) | 1.7 | 2.1 |
| Metal Volume-per-Area (cc/m$^2$) | 1.4 | 2.6 |
| Pore Volume-per-Area (cc/m$^2$) | 16.2 | 1.2 |
| Substrate Vol % of Structure | 9 v % | 36 v % |

TABLE 4-continued

Mass- and Volume-Based Composition

| Property | NPG/ePTFE | CPS/ePTFE |
|---|---|---|
| Metal Vol % of Structure | 7 v % | 44 v % |
| Pore Vol % of Structure, or "Porosity" | 84 v % | 20 v % |

TABLE 5

Electrical and Electrochemical Properties

| Property | NPG/ePTFE | CPS/ePTFE |
|---|---|---|
| Sheet Resistance (ohms/square) | 0.3 | 0.1 |
| Double Layer Capacitance (μF/cm$^2$) | 1875 | 6750 |
| Roughness Factor (m$^2_{ECSA}$/m$^2_{geometric}$) | 29 | 111 |
| Specific ECSA of Metal (m$^2_{ECSA}$/g$_{metal}$) | 1.0 | 4.0 |

TABLE 6

Pore Size of the Metal Phase

| Property | NPG/ePTFE | CPS/ePTFE |
|---|---|---|
| Maximum Pore Size (nm) | 604 | 108 |
| Minimum Pore Size (nm) | 13 | 6 |
| Center of Pore Size Range (nm) | 308 | 57 |
| Median Pore Size (nm) | 32 | 15 |
| Mode of Number-Based Pore Size Distribution (nm) | 16 | 10 |
| Mode of Volume-Based Pore Size Distribution (nm) | 604 | 25 |
| Average of Number-Based Pore Size Distribution (nm) | 54 | 16 |
| Average of Volume-Based Pore Size Distribution (nm) | 375 | 37 |

TABLE 7

Shifts in Pore Size Measurements

| Property | NPG/ePTFE | CPS/ePTFE |
|---|---|---|
| *Shift in Mode from Number-Basis → Volume-Basis Pore Size Distribution* | | |
| Absolute (nm) | 588 | 15 |
| Percent (%) | 3675% | 150% |
| Ratio, Volume/Number (nm$_{volume}$/nm$_{Number}$) | 37.8 | 2.5 |
| *Shift in Average from Number-Basis → Volume-Basis Pore Size Distribution* | | |
| Absolute (nm) | 321 | 21 |
| Percent (%) | 594% | 131% |
| Ratio, Volume/Number (nm$_{volume}$/nm$_{Number}$) | 6.9 | 2.3 |
| *Shift from Median to Average for Number-Basis Pore Size Distribution* | | |
| Absolute (nm) | 22 | 1 |
| Percent (%) | 69% | 7% |
| Ratio, Average/Median (nm$_{Average}$/nm$_{Median}$) | 1.7 | 1.1 |
| *Shift from Mode to Average for Number-Basis Pore Size Distribution* | | |
| Absolute (nm) | 38 | 6 |
| Percent (%) | 238% | 60% |
| Ratio, Average/Mode (nm$_{Average}$/nm$_{Mode}$) | 3.4 | 1.6 |

What is claimed is:

1. A composite material comprising:
a porous polymer substrate, and
a nanoporous metal present within the porous polymer substrate and comprising a number-based nanopore size distribution and a volume-based nanopore size distribution, wherein an average of the volume-based pore size distribution is at least 200% greater than an average of the number-based nanopore size distribution.

2. The composite material of claim 1, wherein the porous polymer substrate comprises a plurality of nodes and a plurality of fibrils that cooperate to define a plurality of interconnected pores, wherein the nanoporous metal is contained at least partially in the pores between the nodes and the fibrils.

3. The composite material of claim 1, wherein the nanoporous metal comprises nanopores of about 10 nm to about 200 nm in size.

4. The composite material of claim 1, wherein the porous polymer substrate comprises a fluoropolymer or a polyolefin.

5. The composite material of claim 4, wherein the porous polymer substrate comprises expanded polytetrafluoroethylene or expanded polyethylene.

6. The composite material of claim 1, wherein the nanoporous metal comprises platinum, iridium, palladium, gold, silver, copper, nickel, or combinations or alloys thereof.

7. The composite material of claim 1, wherein:
the nanoporous metal comprises nanopores of about 1 nm to about 500 nm in average diameter;
the porous polymer substrate comprises micropores that are larger than the nanopores of the nanoporous metal.

8. The composite material of claim 1, wherein the average of the volume-based pore size distribution is at least 500% greater than the average of the number-based nanopore size distribution.

9. The composite material of claim 8, wherein the number-based nanopore size distribution is unimodal and right-skewed.

10. An electrochemical cell comprising the composite material of claim 1.

11. A composite material comprising:
a microporous polymer substrate comprising a plurality of interconnected micropores; and
a nanoporous metal at least partially contained in the micropores of the microporous polymer substrate and separated from the microporous polymer substrate to define gaps.

12. The composite material of claim 11, wherein the microporous polymer substrate is one of a membrane, a tube, and a fiber.

13. The composite material of claim 11, wherein the microporous polymer substrate comprises a fluoropolymer or a polyolefin.

14. The composite material of claim 13, wherein the microporous polymer substrate comprises expanded polytetrafluoroethylene or expanded polyethylene.

15. The composite material of claim 11, wherein the nanoporous metal has a unimodal and right-skewed number-based nanopore size distribution.

16. The composite material of claim 11, wherein the nanoporous metal comprises nanopores of about 10 nm to about 200 nm in size.

17. The composite material of claim 11, wherein the gaps are accessible at a surface of the composite material in a z-direction and the nanoporous metal provides conductivity in at least a x-y direction.

18. A composite material comprising:
a first continuous network comprising a microporous polymer having a plurality of interconnected micropores; and
a second substantially continuous network comprising a nanoporous metal, the second substantially continuous network interpenetrating the first continuous network, wherein the composite material has a porosity of at least 30 vol. %.

19. The composite material of claim 18, wherein the first continuous network includes an interface region that is unmetallized and distinct from the second substantially continuous network.

20. The composite material of claim 19, wherein the interface region is a non-laminated, integral portion of the first continuous network.

21. The composite material of claim 18, wherein the nanoporous metal is separated from the microporous polymer to define gaps.

22. The composite material of claim 17, wherein at least 99 wt. % of the nanoporous metal is retained in the composite material after 1 day of a wet flex particulation test.

23. The composite material of claim 17, wherein at least 99.9 wt. % of the nanoporous metal is retained in the composite material after 1 day of the wet flex particulation test.

24. The composite material of claim 17, wherein the nanoporous metal accounts for less than 40 vol. % of the composite material.

* * * * *